(12) United States Patent
Sheu et al.

(10) Patent No.: US 7,585,846 B2
(45) Date of Patent: Sep. 8, 2009

(54) COMPOUNDS FOR DELIVERING AMINO ACIDS OR PEPTIDES WITH ANTIOXIDANT ACTIVITY INTO MITOCHONDRIA AND USE THEREOF

(75) Inventors: Shey-Shing Sheu, Pittsford, NY (US); Marion W. Anders, Pittsford, NY (US); Lin Xu, Lexington, MA (US); Virendra K. Sharma, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/580,803

(22) PCT Filed: Nov. 26, 2004

(86) PCT No.: PCT/US2004/039739

§ 371 (c)(1),
(2), (4) Date: Nov. 24, 2006

(87) PCT Pub. No.: WO2005/051978

PCT Pub. Date: Jun. 9, 2005

(65) Prior Publication Data

US 2007/0099845 A1 May 3, 2007

Related U.S. Application Data

(60) Provisional application No. 60/524,833, filed on Nov. 25, 2003.

(51) Int. Cl.
| | | |
|---|---|---|
| *A61K 37/00* | (2006.01) | |
| *A61K 31/24* | (2006.01) | |
| *C07C 229/00* | (2006.01) | |
| *C07C 205/00* | (2006.01) | |
| *C07C 261/00* | (2006.01) | |
| *C07C 269/00* | (2006.01) | |
| *C07C 271/00* | (2006.01) | |

(52) U.S. Cl. .................. 514/19; 514/540; 560/19; 560/22; 560/155; 560/159

(58) Field of Classification Search ................ None
See application file for complete search history.

(56) References Cited

U.S. PATENT DOCUMENTS

| | | | |
|---|---|---|---|
| 5,869,456 A | 2/1999 | Levy et al. | |
| 6,197,749 B1 | 3/2001 | Hamuro et al. | |
| 6,331,532 B1 | 12/2001 | Murphy et al. | |
| 6,369,106 B1 | 4/2002 | Atlas et al. | |
| 6,472,378 B2 * | 10/2002 | von Borstel | 514/50 |
| 2001/0005719 A1 * | 6/2001 | Von Borstel | 514/49 |

FOREIGN PATENT DOCUMENTS

GB 2368339 A 5/2002

OTHER PUBLICATIONS

Kanaoka et al. (I), "Chemical Studies on Amino Acids and Peptides. II. Synthesis of Choline Esters of Peptides Related to Tetragastrin," Chemical and Pharmaceutical Bulletin, 26(2), 605-610 (Feb. 1978).*
Kanaoka et al. (II), "Chemical Studies on Amino Acids and Peptides. III. 4,5-Diaryl-4-oxazoline-2-one Derivatives as an Amino Protecting Group," Chemical and Pharmaceutical Bulletin, 26(2), 660-664 (Feb. 1978).*
Pearson et al., "Trialkylsilanes as Scavengers for the Trifluoroacetic Acid Deblocking of Protecting Groups in Peptide Synthesis," Tetrahedron Letters, 30(21), 2739-2742 (1989).*
Aldrich Handbook of Fine Chemicals and Laboratory Equipment, 2000-2001, Milwaukee, WI, see pp. 484-485 (e.g. "cysteine," etc.).*
Database Biosis Accession No. PREV198069011751, Chemical and Pharmaceutical bulletin (Tokyo) 1978 Abstract.
Mehta et al., "Improved Efficiency and Selectivity in Peptide Synthesis:Use of Triethylsilane as a Carbocation Scavenger in Deprotection of t-Butyl Esters and t-Butoxycarbonyl-Protected sites", Tetrahedron Letters 1992 33 (37):5441-5444.
Murphy et al., "Drug delivery to mitochondria:the key to mitochondrial medicine", Advanced Drug Delivery Reviews 2000 41:235-250.
O'Donovan et al., "Mitochondrial Glutathione and Oxidative Stress:Implications for Pulmonary Oxygen Toxicity in Premature Infants", Molecular Genetics and Metabolism 2000 71:352-358.
Vrablic et al., "Altered mitochondrial function and overgeneration of reactive oxygen species precede the induction of apoptosis by 1-O-octadecyl-2-methyl-rac-glycero-3-phosphochooline in p53-defective hepatocytes", FASEB J. 2001 15:1739-1744.

* cited by examiner

*Primary Examiner*—L. E. Crane
(74) *Attorney, Agent, or Firm*—Licata & Tyrrell P.C.

(57) ABSTRACT

Disclosed are hydrophilic choline/N-heterocycle ester compounds containing single amino acids, peptides, or derivatives thereof which have the potential to express anti-oxidant activity capable of reducing reactive oxygen species in cells. These compounds may be used to inhibit oxidative stress-induced cell injury or death both in vivo and ex vivo. In addition, methods for the synthesis of these compounds are disclosed.

15 Claims, 14 Drawing Sheets

| ANTIOXIDANT PRETREATMENT | TIME OF ONSET OF DEPOLARIZATION (MIN) |
|---|---|
| NONE (CONTROL) | 8.1 ± 1.4 |
| GSH | 9.2 ± 2.6 |
| Mito GSH | 17.5 ± 2.1* |
| NAC | 10.5 ± 1.9 |
| Mito NAC | 20.5 ± 3.6* |

COMPOUNDS FOR DELIVERING AMINO ACIDS OR PEPTIDES WITH ANTIOXIDANT ACTIVITY INTO MITOCHONDRIA AND USE THEREOF

CROSS REFERENCE TO RELATED APPLICATIONS

This application claims benefit of PCT/US2004/039739, filed Nov. 26, 2004, which claims benefit of U.S. Provisional Patent Application Ser. No. 60/524,833, filed Nov. 25, 2003, which is hereby incorporated by reference in its entirety.

FIELD OF THE INVENTION

The present invention generally relates to the field of cellular biology and the role of intracellular mitochondria in cellular homeostasis and cytoprotection. More specifically, the present invention is directed to compounds and compositions with mitochondria-specific anti-oxidant potential. The invention also relates to methods of inhibiting and treating oxidative stress-induced cellular morbidity and mortality with the compounds and compositions of this invention.

BACKGROUND OF THE INVENTION

Mitochondrial occupy a central role in cellular homeostasis, particularly by satisfying cellular energy needs, and, paradoxically, also occupy a central role in a range of disease processes. Mitochondria are the major source (>90%) of adenosine triphosphate ("ATP"), which is used in a range of energy-requiring biochemical and homeostatic reactions in the body. Mitochondria are also a major source of reactive oxygen species ("ROS"), which are involved in the etiology and progression of a range of disease processes, including, for example, inflammation, stroke, cardiovascular disease, cancer, diabetes, neurodegenerative diseases (e.g., Alzheimer's Disease, Parkinson's Disease), drug- and chemical-induced toxicity, alcohol-induced liver damage, and aging-related diseases.

Antioxidant mechanisms in the body counteract the deleterious effects of ROS. These antioxidant mechanisms may, however, be overwhelmed during the development and progression of disease processes. The hydrophilic tripeptide glutathione (L-γ-glutamyl-L-cysteinylglycine) is an important antioxidant compound. Unlike lipophilic antioxidants, which must be provided by the diet, glutathione is synthesized in the body, particularly in the liver. Glutathione is present in mitochondria, but mitochondria lack the enzymes needed for the synthesis of glutathione (Griffith and Meister, "Origin and Turnover of Mitochondrial Glutathione," *Proc. Natl. Acad. Sci. USA* 82:4668-4672 (1985)), and the mitochondrial glutathione pool is maintained by transport from the cytosol into the mitochondria. The mitochondrial glutathione pool amounts to approximately 15% of total cellular glutathione (Meredith and Reed, "Status of the Mitochondrial Pool of Glutathione in the Isolated Hepatocyte," *J. Biol. Chem.* 257: 3747-3753 (1982)). Although the mitochondrial glutathione pool is relatively small, it plays a key role in cytoprotection against ROS, and the depletion of mitochondrial glutathione concentrations is associated with cell damage and death (Meredith and Reed, "Depletion in vitro of Mitochondrial Glutathione in Rat Hepatocytes and Enhancement of Lipid Peroxidation by Adriamycin and 1,3-bis(2-chloroethyl)-1-nitrosourea (BCNU)," *Biochem. Pharmacol.* 32:1383-1388 (1982); Shan et al., "Selective Depletion of Mitochondrial Glutathione Concentrations by (R,S)-3-hydroxyl-4-pentenoate Potentiates Oxidative Cell Death.," *Chem. Res. Toxicol.* 6:75-81 (1993); Hashmi et al., "Enantioselective Depletion of Mitochondrial Glutathione Concentrations by (S)- and (R)-3-hydroxy-4-pentenoate," *Chem. Res. Toxicol.* 9:361-364 (1996)). In particular, depletion of mitochondrial glutathione concentrations sensitizes organs to cytokine (TNF)-associated cell damage (Colell et al., "Hepatic Mitochondrial Glutathione Depletion and Cytokine-mediated Alcoholic Liver Disease," *Alcohol Clin. Exp. Res.* 22:763-765 (1998); Colell et al., "Selective Glutathione Depletion of Mitochondria by Ethanol Sensitizes Hepatocytes to Tumor Necrosis Factor," *Gastroenterology* 115:1541-1551 (1998)). The antioxidant activity of glutathione is associated with its thiol group.

SUMMARY OF THE INVENTION

A first aspect of the present invention relates to a compound according to formula (I) or formula (II)

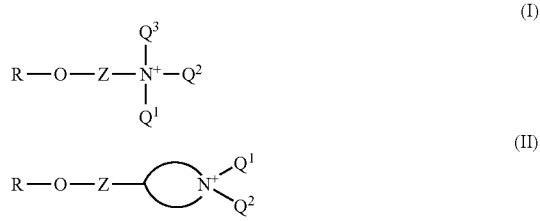

wherein for both formula (I) and formula (II)
R is (i) an amino acid or amino acid derivative having antioxidant activity, or
(ii) a peptide comprising two or more amino acids or amino acid derivatives, wherein the peptide has antioxidant activity;
Z is a linker molecule containing 1 to about 20 atoms in a direct chain;
$Q^1$, $Q^2$, and $Q^3$ are independently aliphatic C1 to C5 hydrocarbons, or $Q^2$ and $Q^3$ together form an aliphatic N-heterocycle; and wherein for formula (II), the N-heterocycle possesses a quaternary nitrogen and $Q^2$ is optional.

A second aspect of the present invention relates to a pharmaceutical composition that includes a pharmaceutically acceptable carrier and a compound according to the first aspect of the present invention.

A third aspect of the present invention relates to a method of inhibiting oxidative stress-induced cell injury and/or death that includes providing a compound according to the first aspect of the present invention and contacting a cell with the compound, whereby the compound is taken up by the cell and enters mitochondria of the cell, thereby scavenging oxidative free radicals and/or reactive oxygen species to inhibit oxidative stress-induced cell injury and/or death.

A fourth aspect of the present invention relates to a method of treating a condition associated with oxidative stress-induced cell injury and/or death that includes providing a compound according to the first aspect of the present invention and administering the compound to a patient having a condition associated with oxidative stress-induced cell injury and/or death, whereby the compound is taken up by cells at risk of oxidative stress-induced injury and/or death, and enters mitochondria of the cells to inhibit oxidative stress-induced injury and/or death thereof, thereby treating the condition.

A fifth aspect of the present invention relates to a method of making a compound of formula (I) or formula (II) by reacting an intermediate according to formula (III) or formula (IV),

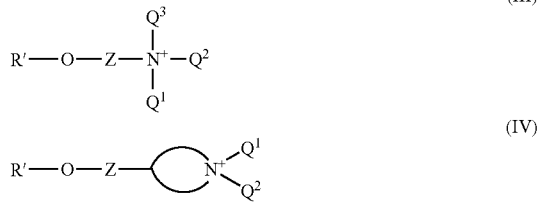

wherein R' is a derivative of R having one or more protecting groups, with one or more agents that are effective to remove the one or more protecting groups, thereby forming the compound of formula (I) or the compound of formula (II), respectively.

The primary native mitochondrial mechanisms for counteracting the deleterious effects of ROS involve glutathione and derivatives thereof. Since mitochondria do not have the enzymes necessary for the synthesis of glutathione, the mitochondrial glutathione pool must be maintained. Mitochondrial transport systems and the mitochondrial electrochemical potential gradient provide mechanisms to concentrate hydrophilic, positively charged derivatives of glutathione in mitochondria Choline transporters are well known. (Apparsundaram et al., "Molecular Cloning of a Human, Hemicholinium-3-sensitive Choline Transporter," *Biochem. Biophys. Res. Commun.* 276:862-867 (2000); Okuda et al. "Identification and Characterization of the High-Affinity Choline Transporter," *Nat. Neurosci.* 3:120-125 (2000); Porter et al., "Choline Transport into Rat Liver Mitochondria: Characterization and Kinetics of a Specific Transporter," *J. Biol. Chem.* 267: 14637-14646 (1992), each of which is hereby incorporated by reference in its entirety). Hence, the focus of the invention is to exploit the characteristics of these transporters and of the mitochondrial electrochemical potential gradient to concentrate hydrophilic choline/N-heterocycle esters of glutathione and other peptide- and amino acid-based antioxidants in mitochondria, and thereby provide critical mitochondrial antioxidant potential to counteract the effect of ROS. As demonstrated by the Examples, the compounds of the present invention afford cytoprotection to cultured cells and cells in vivo exposed to oxidative stress.

BRIEF DESCRIPTION OF THE DRAWINGS

FIG. 3A shows the loss of neuronal morphology and condensed fragmented nuclei (arrows) upon treatment with 250 μM $H_2O_2$. FIG. 3B is a control for FIG. 3A. FIG. 3C is a bar diagram summary of the percent of neurons with condensed fragmented nuclei after $H_2O_2$ treatment. The concentrations of $H_2O_2$ used are shown on the x-axis. FIG. 3C also shows an increased percentage of # condensed nuclei upon 3-HP treatment, which depletes mitochondrial GSH. FIGS. 3D and 3E demonstrate mitochondrial staining via cytochrome C immunoreactivity (1:500) and COX Vi immunoreactivity (1:250), respectively, both demonstrating punctuate fluorescence pattern indicative of mitochondrial staining.

FIG. 4A shows TMRE-labeled spinal cord neurons at time 0 (panel A1) and at time +20 minutes (panel A2), indicating consistent mitochondrial morphology. FIG. 4B shows image pairs collected with similar parameters as FIG. 5A, however FIG. 4B shows before (panel 1) and after (panel 2) treatment with $H_2O_2$, respectively. Of note is the significant loss of TMRE-fluorescence in neurons and loss of mitochondrial morphology in these $H_2O_2$ treated cells. FIG. 4C quantifies TMRE-fluorescence as ΔF/Fo as a function of time after exposure to 3 μM and 3 mM concentrations of $H_2O_2$. The different traces indicate different mitochondrion within the same neuronal some FIG. 4D quantifies TMRE-fluorescence as ΔF/Fo as a function of time after exposure to $H_2O_2$, except that the signals are from two different neuronal soma (N1, N2) and four neuritis (n1-n4). Of note is the considerable heterogeneity of response.

FIG. 5C demonstrates MCIB fluorescence from another field after treatment with saponin (0.2 μg/ml×20 s). The treatment reduces signal from cytoplasmic GSH leaving a more punctuate fluorescence pattern in mitochondrial GSH.

DETAILED DESCRIPTION OF THE INVENTION

Figure 1:
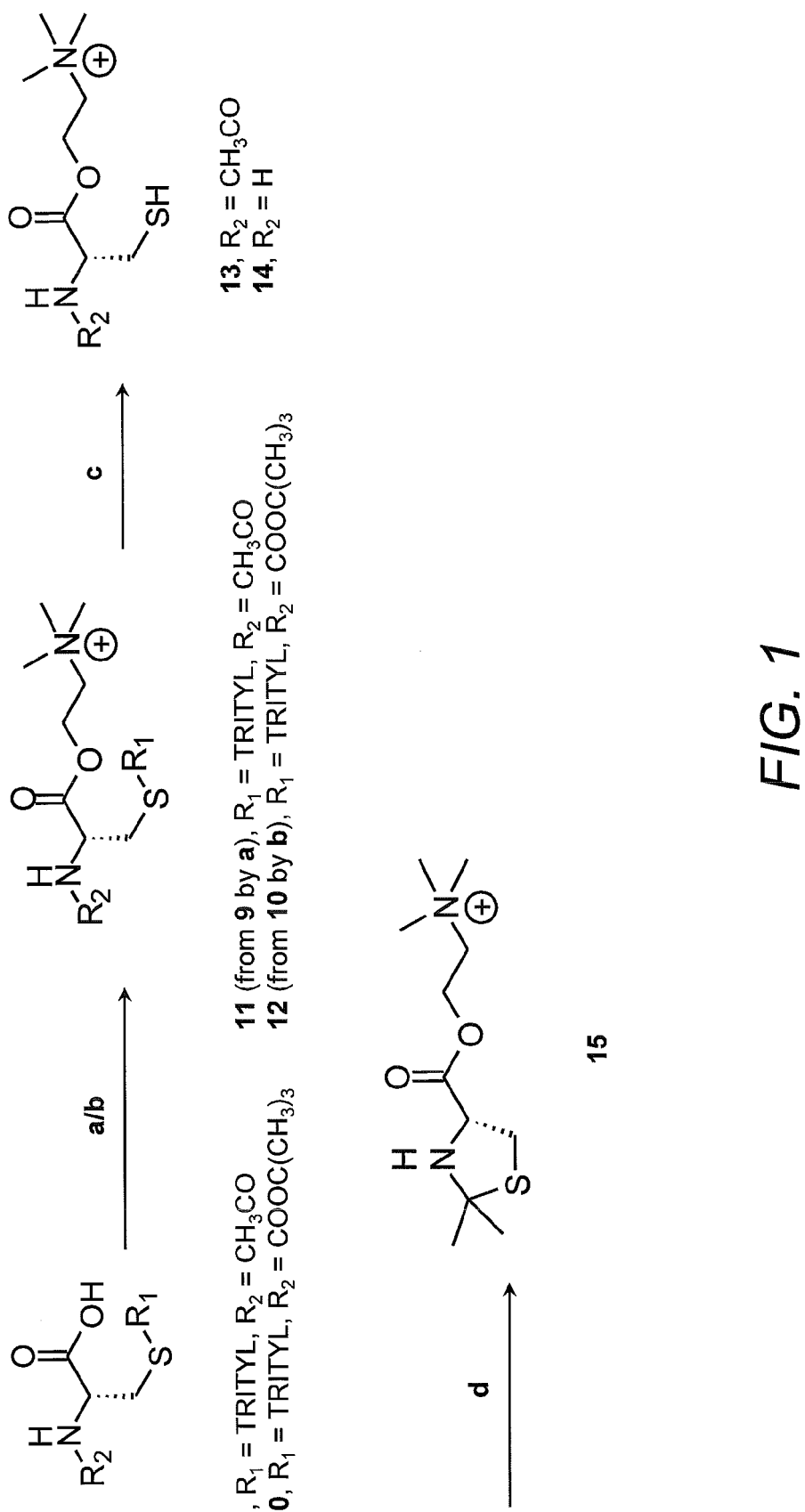
FIG. 1 shows a method for the synthesis of N-acetyl L-cysteine choline ester (compound 13), L-cysteine choline ester (compound 14) and its derivative (D)-2-(trimethylamino) ethyl-2,2-dimethylthiazolidine-4-carboxylate (compound 15). a: to 9, DCC, and 4-dimethylamino pyridine/4-dimethylamino pyridinium chloride in $CH_2Cl_2$, was added 2-bromoethanol with stirring for 12 hours at room temperature. Trimethylamine was subsequently added to the resulting solution of 2-acetylamino-3-tritylsulfanyl-L-propionic acid 2-bromo-ethyl ester in THF with stirring for 48 hours at room temperature. b: to 10, DCC, 4-dimethylamino pyridine and 4-dimethylamino pyridinium chloride in $CH_2Cl_2$ was added 2-(dimethylamino)ethanol with stirring for 12 hours at room temperature. Methyl iodide was subsequently added to the resulting solution of 2-tert-butoxycarbonylamino-3-tritylsulfanyl-L-propionic acid 2-dimethylamino-ethyl ester in THF with stirring for 12 hours at room temperature. c: to 11 or 12 in $CH_2Cl_2$ was added $Et_3SiH$ and anhydrous $CF_3COOH$ with stirring at room temperature for 1 hour. d: acetone.

The present invention relates to compounds that are readily taken up by cells and the mitochondria inside the cells, where the compounds can exert their effect as antioxidants, reducing the reactive oxygen species (ROS) that are generated in mitochondria following ROS-inducing events. In particular, the compounds of the present invention are particularly useful to reduce ROS that occur following trauma or other events capable of inducing apoptosis, including excitotoxic apoptosis.

The compounds of the present invention include those provided by formula (I) and formula (II) below:

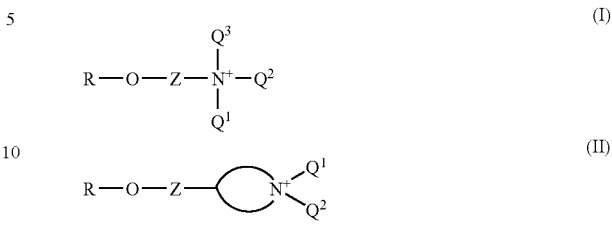

wherein for both formula (I) and formula (II),

R is an moiety having antioxidant activity, preferably either (i) an amino acid or amino acid derivative having antioxidant activity, or (ii) a peptide including two or more amino acids or amino acid derivatives, wherein the peptide has antioxidant activity;

Z is any linker group; and $Q^1$, $Q^2$, and $Q^3$ are independently aliphatic C1 to C5 hydrocarbons, or $Q^2$ and $Q^3$ together form an aliphatic N-heterocycle; and wherein for formula (II), the N-heterocycle possesses a quaternary nitrogen and $Q^2$ is optional.

In the compounds of the present invention, the R group is intended to provide antioxidant activity capable of reducing ROS in cells. The R group can be any individual amino acid or amino acid derivative that possesses such antioxidant activity, or the R group can be a peptide that contains one or more amino acids or amino acid derivatives that possess such antioxidant activity. The amino acids and their derivatives that form the R group can be L-amino acids or derivatives thereof, D-amino acids or derivatives thereof, or combinations thereof.

According to one embodiment of the present invention, the R group is a single amino acid or derivative thereof. Exemplary amino acids and derivatives thereof include, without limitation, glutamic acid, cysteine, N-acetyl-cysteine, glycine, and 2,2-dialkylthiazolidine-4-carboxylic acid.

According to another embodiment of the present invention, the R group is a peptide, preferably a peptide containing from two up to about ten amino acids or derivatives thereof, preferably from two up to about five amino acids or amino acid derivatives. Exemplary peptide R groups include, without limitation, L-γ-glutamylcysteine, L-γ-glutamylglycine, L-cysteinylglycine, glutathione, L-carnosine, L-carnitine, and acetyl-L-carnitine.

The Z group can be any linker molecule that does not interfere with the antioxidant activity of the R group and does not interfere with the polarity of the compound caused by the presence of the quaternary nitrogen. The Z group preferably contains up to and including about 20 molecules in a direct chain (i.e., excluding molecules in any sidechains) that links together the O and the quaternary nitrogen or the heterocycle that contains therein the quaternary nitrogen. Exemplary Z groups include, without limitation, $-Z^1-Z^2-$, $-Z^1-O-Z^2-$, $-Z^1-S-Z^2-$, $-Z^1-N(H)-Z^2-$, $-Z^1-CO-N(H)-Z^2-$, or $-Z^1-N(H)-CO-Z^2-$ where $Z^1$ is a direct link, an aliphatic or non-aliphatic C1 to C10 hydrocarbon, a single, fused or multi-ring aromatic, or an aliphatic or non-aliphatic cyclic group; and where $Z^2$ is an aliphatic or non-aliphatic C1 to $C_{10}$ hydrocarbon, a single, fused or multi-ring aromatic, or an aliphatic or non-aliphatic cyclic group.

As used to define the Z groups, the term "aliphatic or non-aliphatic C1 to C10 hydrocarbon" refers to both alkylene groups that contain a single carbon and up to about 10 carbons, as well as alkenyl groups and an alkynyl groups that contain two carbons and up to about 10 carbons, whether the carbons are present in a single chain or a branched chain. Exemplary aliphatic or non-aliphatic C1 to C10 hydrocarbon include, without limitation, methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene, 3-butynylene, etc.

As used to define the Z groups, the term "single, fused or multi-ring aromatic" refers to any combination of aromatic ring structures, whether or not the ring(s) contain heteroatoms. Exemplary single, fused or multi-ring aromatics include, without limitation, phenyl, biphenyl, triphenyl, napthyl, phenanthryl, anthracyl, etc.

As used to define the Z groups, the term "aliphatic or non-aliphatic cyclic group" refers to any non-aromatic cyclic structure, whether or not the cyclic structure contains one or more hetero-atoms. Exemplary aliphatic or non-aliphatic cyclic groups include, without limitation, aliphatic hydrocarbon cyclic structures such as cyclopentyl, cyclohexyl, cycloheptyl, etc., and non-aromatic hydrocarbon cyclic structures such as cyclopentenyl, cyclohexenyl, cyclopentadienyl, cyclohexadienyl, etc. Exemplary aliphatic or non-aliphatic heterocyclic groups include, without limitation, aliphatic or non-aliphatic N-heterocycles (e.g., aza- and diaza-cycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, etc.), aliphatic or non-aliphatic S-heterocycles (e.g., thiranyl, thietanyl, tetrahydrothiophenyl, dithiolanyl, tetrahydrothiopyranyl, thiophenyl, thiepinyl, thianaphthenyl, etc.), and mixed heterocycles such as morpholinyl, thioxanyl, thiazolyl, isothiazolyl, thiadiazolyl, etc.

The various Q groups ($Q^1$, $Q^2$, and $Q^3$) are individually (i.e., independent of one another) aliphatic C1 to C5 hydrocarbons, such as methyl, ethyl, propyl, butyl, and pentyl groups; alternatively, for compounds of formula (I), $Q^2$ and $Q^3$ together can form an aliphatic N-heterocycle, such as a N-cyclopentyl, N-cyclohexyl, etc.

With respect to the compounds according to formula (II), the N-heterocycle containing a quaternary nitrogen can be any such heterocycle. Exemplary N-heterocycles containing a ring nitrogen that can be in a quaternary state include, without limitation, (i) rings with the nitrogen double-bonded within the ring structure (in which case $Q^2$ is not present), such as pyridinyl, pyrimidinyl, quinolinyl, isoquinolinyl, imidazolyl, pyrazolyl, pirazinyl, etc.; and (ii) rings with the nitrogen only single-bonded within the ring structure (in which case both $Q^1$ and $Q^2$ are both present), such as pyrrolyl, pyrrolidinyl, morpholinyl, piperidinyl, etc. Other such N-heterocyles that are known in the art can form the ring system in compounds of formula II (see e.g., *Handbook of Chemistry and Physics*, 63 ed., at page C-35 et seq.).

Particularly preferred compounds of the present invention include, without limitation, the following: L-γ-glutamyl-L-cysteinylglycine choline ester, D-γ-glutamyl-L-cysteinylglycine choline ester, L-cysteine choline ester, L-γ-glutamyl-L-cysteine choline ester, D-γ-glutamyl-L-cysteine choline ester, N-acetyl-L-cysteine choline ester, D-2-(trimethylamino) ethyl-2,2-dimethylthiazolidine-4-carboxylic acid, and L-2-(trimethylamino)ethyl-2,2-dimethylthiazolidine-4-carboxylic acid, [2-(2-acetylamino-3-mercapto-propionyloxy)-ethyl]-trimethyl-ammonium bromide, [2-(2)-amino-3-mercapto-propionyloxy)-ethyl]-trimethyl-ammonium iodide, (2-{2-[2-(4-amino-4-carboxy-butyrylamino)-3-mercapto-propionylamino]-acetoxy}-ethyl)-trimethyl-ammonium bromide, 2-amino-3-mercapto-propionic acid-2-dimethylamino-ethyl ester.

According to one embodiment, the compound can be any compound encompassed by the formula (I) or formula (II) above, except that the compound is not glycine choline ester.

The compounds of the present invention can also be in the form of a salt, preferably a pharmaceutically acceptable salt. The term "pharmaceutically acceptable salt" refers to those salts that retain the biological effectiveness and properties of the free bases or free acids, and which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

The above-identified compounds, or their salts, can be prepared according to various procedures using different starting materials and reactants, as identified below by way of example.

According to one approach, a final intermediate according to formula (III) or formula (IV), wherein R' is a derivative of R having one or more protecting groups, is reacted with one or more agents that are effective to remove the one or more protecting groups, thereby forming the compound of formula (I) or the compound of formula (II), respectively

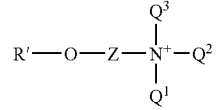  (III)

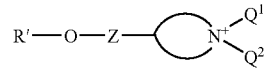  (IV)

According to a preferred approach, the intermediate according to formula (III) or formula (IV) is first exposed to trifluoroacetic acid under conditions effective to remove the one or more protecting groups (i.e., deprotect the intermediate), and subsequently exposed to a cation scavenger agent, such as triethyl silane, to form the compounds according to formula (I) or formula (II). Removal of the protecting groups can be carried out under any suitable conditions known to those of skill in the art, but preferably using either trifluoroacetic acid in dichloromethane, hydrogen bromide or hydrogen chloride in acetic acid, or tri-n-butyl phosphine.

Intermediate (III) can be prepared according to any one of several exemplary approaches. In a first approach, an intermediate according to formula (V)

  (V)

is reacted with $Q^1$-N($Q^2$)-$Q^3$ under conditions effective to form the intermediate according to formula (III). As an alternative to the intermediate of formula (V), its homologs containing iodine or chlorine can also be used. Typically, this step is performed in THF at room temperature for a sufficient amount of time (i.e., overnight up to about 48 hours). The intermediate of formula (V) and its homologs are prepared by reacting an intermediate according to formula (VI)

R'—OH  (VI)

with HO-Z-Br (or HO-Z-I or HO-Z-Cl) under conditions effective to form the intermediate according to formula (V) or its homologs. Exemplary conditions include the use of (i) DCC or DIC and 4-dimethylaminopyridine followed by (ii) dichloromethane at room temperature for about 6 to 24 hours, preferably about 12 hours.

In a second approach, the intermediate according to formula (III) is prepared by reacting an intermediate according to formula (VII) with

(VII)

with I-$Q^1$ under conditions effective to form the intermediate according to formula (III). Typically, this step is performed in ethyl acetate for a sufficient amount of time (i.e., overnight up to about 48 hours).

In a third approach, where the compound to be prepared is a protected glutathione choline ester, the synthesis can be carried out by reacting N-trimethyl-alkyl glycine ester with protected L-γ-glutamyl-L-cysteine under conditions effective to form the intermediate according to formula (III). This can be achieved according to the synthesis procedure described in Example 2, infra.

The intermediate according to formula (IV) is prepared by reacting an intermediate according to formula (VIIIa) or (VIIIb) with

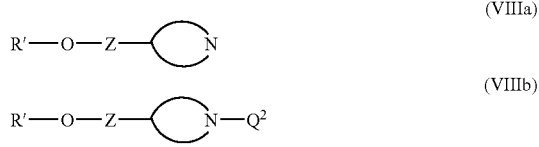

(VIIIa)

(VIIIb)

with I-$Q^1$ under conditions effective to form the intermediate according to formula (IV). Typically, this step is performed in ethyl acetate for a sufficient amount of time (i.e., overnight up to about 48 hours).

The intermediates according to formula (VII) and formula (VIIIa) or (VIIIb) can be prepared by reacting an intermediate R'—OH with either HO-Z-N($Q^2$)-$Q^3$ or HO-Z-(N-heterocyclic amine) or HO-Z-(N-heterocyclic amine)-Q2 under conditions effective to form the intermediate according to formula (VII) or formula (VIII), respectively. Exemplary conditions include the use of (i) DCC or DIC and 4-dimethylaminopyridine followed by (ii) dichloromethane at room temperature for about 6 to 24 hours, preferably about 12 hours.

For the compounds according to formula (I) or (II) where R is L-cysteine, the dimethylthiazolidine derivative thereof can be prepared by treating the compound(s) with acetone under effective conditions. Such a compound according to formula (I) is (R)-2-(trimethylamino)ethyl-2,2-dimethylthiazolidine-4-carboxylic acid.

Having prepared the compounds of the present invention, such compounds can be used in forming a pharmaceutical composition that is intended for therapeutic uses of the type described hereinafter. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. For example, application to mucous membranes and/or lungs can be achieved with an aerosol or nebulized spray containing small particles of a compound of this invention in a spray or dry powder form.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy us of a syringe exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container or metered dose inhaler together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention, by virtue of their charge carried by the quaternary nitrogen, are believed to be more readily taken up by cells and, in particular, mitochondria within such cells. Without being bound by belief, it is expected that the compounds of the present invention are transported passively through the mitochondrial membrane, achieving delivery of the R group therein, which possesses antioxidant activity and can therefore be used to inhibit the effects of ROS in mitochondria.

Therefore, one aspect of the present invention relates to a method of inhibiting oxidative stress-induced injury and/or death of a cell. Basically, a cell, whether located in vitro or in vivo, is contacted with the compound or its salt (as well as a pharmaceutical composition of the present invention), whereby the compound, presumably by virtue of its charged quaternary nitrogen, is taken up by the cell and enters mitochondria of the cell. As a result of its entry in the cell and accumulation within the mitochondria, the R group carried by the compound is able to exert its antioxidant activity within the mitochondrial environment, scavenging oxidative free radicals and/or reactive oxygen species to inhibit oxidative stress-induced injury and/or death. The cells to be treated in accordance with this aspect of the present invention can be any cell that possesses mitochondria, but preferably those mitochondria-containing cells that have a significant population of mitochondria therein. Exemplary cells include, without limitation, neuronal cells, muscle cells (preferably skeletal or cardiac muscle cells), liver cells, and kidney cells.

By virtue of the ability to inhibit oxidative stress-induced injury and/or death of a cell, the present invention also affords a method of treating or preventing a condition associated with oxidative stress-induced injury and/or death. This aspect of the invention is carried out by administering a compound of the present invention, or its salt (as well as pharmaceutical compositions containing the same) to a patient having a condition associated with oxidative stress-induced cellular injury and/or death. As a result of such administration, the compound is readily taken up by cells at risk of oxidative stress-induced injury and/or death, and enters the mitochondria of such cells. As noted above, entry of the compound into cells and accumulation within the mitochondria allows the R group carried by the compound to exert its antioxidant activity within the mitochondrial environment, scavenging oxidative free radicals and/or reactive oxygen species to inhibit oxidative stress-induced injury and/or death. As a consequence, use of the compound can be used to treat or prevent those conditions associated with oxidative stress-induced injury and/or death.

Administration of the compound (or pharmaceutical composition) can be carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, transmucosally, or via inhalation. Frequently, it will be necessary to repeat administration of the compound or pharmaceutical composition over a time course of several hours, or several days, weeks, or months. If the condition is a chronic condition, then administration may be carried out for an indeterminate period of time.

Conventional administration methods may be suitable for use in the present invention as described below.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art. The quantity of the compound or composition administered will vary depending on the patient and the mode of administration and can be any effective amount. Typical dosages include about 0.01 to about 100 mg/kg·body wt. The preferred dosages include about 0.01 to about 0.1 mg/kg·body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect.

Conditions to be treated or prevented in accordance with this aspect of the present invention are any condition, disease, disorder, or dysfunction that implicates ROS in the etiology of the condition, disease, disorder, or dysfunction. Exemplary conditions, diseases, disorders, and dysfunctions include, without limitation, stroke, neurodegenerative diseases (such as Alzheimer's Disease, Parkinson's Disease, Huntington's Disease, spinocerebellar ataxias), trauma (such as spinal cord injuries, skeletal or cardiac muscle injuries, kidney injuries, or liver injuries), muscular disorders (such as mitochondrial myopathy, lactic acidosis), diabetes, ischemia-reperfusion tissue injury, hypoxic-induced tissue damage, migraines, congenital mitochondrial diseases (such as MELAS, LHON, Kearns-Sayres Syndrome, MERRF, NARP, Leigh's Syndrome), neuromuscular degenerative disorders (such as Friedreich's Ataxia, Duchenne muscular dystrophy, Multiple Sclerosis), epilepsy, neuropathy, neurological and neuropsychological developmental delays, amyotrophic lateral sclerosis (Lou Gehrig's Disease), renal tubular acidosis, and aging related diseases or disorders (such as cognitive and motor disorders, progeria, cancer). While the above list is merely illustrative, a more complete list of mitochondrial diseases or disorders that can be treated in accordance with the present invention is provided in United States Patent Application 2001/0005719 by Von Borstel, which is hereby incorporated by reference in its entirety.

By treating, it is intended that the compounds and compositions of the invention can be used to diminish in whole or in part the symptoms associated with conditions, diseases, disorders, and dysfunctions that implicate mitochondrial oxidative stress. The administration of the compounds and compositions of the invention can, in certain circumstances, effectively minimize tissue damage associated with trauma or other events, or slow the progression of chronic diseases or dysfunctions.

EXAMPLES

The following examples are provided to illustrate embodiments of the present invention but are by no means intended to limit its scope.

Example 1

Synthesis of N-Acetyl L-Cysteine and L-Cysteine Choline Esters, and (R)-[2-(2,2-Dimethyl-thiazolidine-4-carbonyloxy)-ethyl]trimethyl-ammonium chloride All reactions were carried out under dry $N_2$ except where noted. All solvents were distilled from drying agents. Reagents were purchased from Aldrich and VWR. Normal phase column chromatography was performed on Silica Gel 60 (230-400 Mesh, EM Science). Reverse phase column chromatography was performed on Bakerbond™ $C_{18}$ (40 μm, J. T. Baker). $^1H$, $^{13}C$, and COSY NMR data were recorded on a Bruker Avance 400 with $Me_4Si$ as the internal standard except where noted. MS analyses were performed with an Agilent LC/MSD ion-trap mass spectrometer (Agilent Technologies) with an electrospray interface operated in the positive-ion mode.

FIG. 1 shows a preferred method for the synthesis of N-acetyl L-Cysteine Choline Ester.

[2-(2-Acetylamino-3-tritylsulfanyl-L-propionyloxy)-ethyl]-trimethyl-ammonium bromide (11): To a solution of 2-acetylamino-3-tritylasulfanyl-L-propionic acid (9) (2.5 g, 6.26 mmol), DCC (2.58 g, 12.5 mmol), 4-dimethylamino pyridine (1.53 g, 12.5 mmol), and 4-dimethylamino pyridinium chloride (1.99 g, 12.5 mmol) in $CH_2Cl_2$ (50 ml) was added 2-bromo-ethanol (1.33 ml, 18.8 mmol). After stirring for 12 h at room temperature, the mixtures were filtered and extracted with 0.1% HCl, water, and brine subsequently. The extracted $CH_2Cl_2$ solution was dried with anhydrous MgSO4 and evaporated to dryness. The white residue was purified by chromatography on silica gel (ethyl acetate/methanol 45:50) to give 2-acetylamino-3-tritylsulfanyl-L-propionic acid 2-bromo-ethyl ester (2.2 g, 70%) as a white solid; $^1H$ NMR ($CDCl_3$, 400 MHz): 7.40-7.38 (m, 6H), 7.29-7.18 (m, 9H), 6.07 (d, 1H, J=7.77 Hz), 4.55 (dd, 1H, J=6.35 and 4.59 Hz), 4.35 (t, 2H, J=6.94 Hz), 3.41 (t, 2H, J=6.94 Hz), 2.74 (dd, 1H, J=6.35 and 12.5 Hz), 2.61 (dd, 1H, J=4.59 and 12.5 Hz), 1.92 (s, 3H). $^{13}C$ NMR ($CDCl_3$, 100 MHz): 169.9, 169.6, 144.1, 129.3, 127.9, 126.8, 66.9, 64.4, 51.1, 33.5, 28.0, 22.8; Electrospray-ion trap-MS: Calcd for $C_{26}H_{26}BrNO_3S$: m/z 511.1 & 513.1, Found: m/z 534.0 & 535.9 [M+Na]+.

At –78° C., liquid trimethylamine (1 ml, 10.5 mmol) was added to a solution of 2-acetylamino-3-tritylsulfanyl-L-propionic acid 2-bromo-ethyl ester (660 mg, 1.29 mmol) in THF (20 ml). The solution was allowed to warm to room temperature. After stirring for 48 h, the formed white precipitate was filtered and rinsed with THF (5 ml×2) to give products 11 (600 mg, 81%). $^1H$ NMR (DMSO-$d_6$, 400 MHz): δ 7.34-7.22 (m, 15H), 4.40 (t, 2H, J=4.34 Hz), 4.12 (dd, 1H, J=10.9 & 12.2 Hz), 3.66 (t, 2H, J=4.34 Hz), 3.43 (d, 1H, J=3.43 Hz, NH), 3.10 (s, 9H), 2.63 (dd, 1H, J=10.9 & 4.54 Hz), 2.42 (dd, 1H, J=4.54 & 12.2 Hz), 1.85 (s, 3H); $^{13}C$ NMR (DMSO-$d_6$, 100 MHz): δ 170.0, 169.8, 144.3, 129.3, 128.4, 127.2, 66.5, 63.6, 59.0, 53.0, 51.7, 32.6, 22.5; Electrospray-ion trap-MS: Calcd for $C_{29}H_{35}N_2O_3S^+$: m/z 491.2. Found: m/z 491.2 [M]+.

N-acetyl-L-cysteine choline ester (13): To a solution of 11 (400 mg, 0.7 mmol) in $CH_2Cl_2$ (10 ml) was added to $Et_3SiH$ (390 μl, 2.4 mmol) and anhydrous $CF_3COOH$ (3 ml) subsequently. The mixtures were stirred at room temperature for 1 h. The solution was dried under reduced pressure. The oily residue was dissolved into $Et_2O$ (15 ml) and 1% HCl aqueous solution (15 ml). The aqueous solution was separated, rinsed twice with $Et_2O$ (5 ml), neutralized by 10% $NaHCO_3$ to pH 7.0, and then lyophilized. The residue was purified by a preparative reversed-phase C18 column (20 cm×2.5 cm) with 5% $CH_3CN$ in $H_2O$ as eluent to give products 13 as a chloride salt (156 mg, 89%); $^1H$ NMR (DMSO-$d_6$/$D_2O$, 400 MHz): δ 4.56 (t, 1H, J=6.44 Hz), 4.45 (t, 2H, J=3.20 Hz), 3.60 (t, 2H, J=3.20 Hz), 3.10 (dd, 1H, J=6.40 & 10.0 Hz), 3.03 (s, 9H), 2.91 (dd, 1H, J=6.40 & 10.0 Hz), 1.87 (s, 3H); $^{13}C$ NMR (DMSO-$d_6$, 100 MHz): δ 175.3, 172, 65.8, 60.9, 55.3, 53.4, 53.3, 23.2; Electrospray-ion trap-MS: Calcd for $C_{10}H_{21}N_2O_3S^+$: m/z 249.1. Found: m/z 249.0 [M]+.

FIG. 1 also shows a preferred method for the synthesis of L-cysteine choline ester.

[2-(2-tert-Butoxycarbonylamino-3-tritylsulfanyl-L-propionyloxy)-ethyl]-trimethyl-ammonium iodide (12): To a solution of boc-L-Cys(trityl)-OH (10) (2 g, 4.3 mmol), DCC (1.78 g, 8.6 mmol), 4-dimethylamino pyridine (1.05 g, 8.6 mmol), and 4-dimethylamino pyridinium chloride (1.37 g, 8.6 mmol) in $CH_2Cl_2$ (50 ml) was added 2-(dimethylamino) ethanol (1.2 ml, 12 mmol). After stirring for 12 h at room temperature, the mixtures were filtered and extracted with 0.1% HCl, water, and brine subsequently. The extracted $CH_2Cl_2$ solution was dried with anhydrous $MgSO_4$ and evaporated to dryness. The white residue was purified by chromatography on silica gel (ethyl acetate/methanol 65:35) to give 2-tert-butoxycarbonylamino-3-tritylsulfanyl-L-propionic acid 2-dimethylamino-ethyl ester (1.6 g, 67%) as a white solid; $^1H$ NMR ($CDCl_3$, 400 MHz): 7.40-7.38 (m, 6H), 7.25-7.15 (m, 9H), 5.32 (d, 1H, J=8.24 Hz), 4.30 (dd, 1H, J=8.24 & 5.27 Hz), 4.17 (t, 2H, J=5.77 Hz), 2.60 (d, 2H, J=5.27 Hz), 2.49 (t, 2H, J=5.78 Hz), 2.19 (s, 6H), 1.42 (s, 9H); $^{13}C$ NMR ($CDCl_3$, 100 MHz): 170.5, 154.7, 144.0, 129.2, 127.7, 126.5, 79.5, 66.4, 63.1, 57.1, 52.2, 45.4, 33.9, 28.0; Electrospray-ion trap-MS: Calcd for $C_{31}H_{38}N_2O_4S$: m/z 534.3, Found: m/z 535.0 [M+H]+ & 557.1 [M+Na]+.

To a solution of 2-tert-butoxycarbonylamino-3-tritylsulfanyl-L-propionic acid 2-dimethylamino-ethyl ester (1.5 g, 2.8 mmol) in THF (20 ml) was added methyl iodide (0.87 ml, 14 mmol). After stirring for 12 h at room temperature, the mixtures were filtered and rinsed with THF (5 ml×2) to give products 12 as a white solid (2.1 g, 90%); $^1$H NMR (CDCl$_3$, 400 MHz): 7.37-7.20 (m, 15H), 5.09 (d, 1H, J=6.98 Hz, NH), 4.60 (dd, 1H, J=15.2 & 6.40 Hz), 4.47 (dd, 1H, J=15.0 & 4.44 Hz), 4.09 (t, 2H, J=6.63 Hz), 3.95 (dd, 2H, J=4.44 & 6.40 Hz), 3.40 (s, 9H), 2.64 (dd, 2H, J=6.63 Hz) 1.39 (s, 9H); $^{13}$C NMR (CDCl$_3$, 100 MHz): 170.7, 154.7, 143.7, 129.0, 127.8, 126.6, 79.8, 66.7, 64.4, 59.9, 58.5, 54.1, 32.8, 27.9; Electrospray-ion trap-MS: Calcd for $C_{32}H_{41}N_2O_4S^+$: m/z 549.3. Found: m/z 549.1 [M]$^+$.

[2-(2-Amino-3-mercapto-L-propionyloxy)-ethyl]-trimethyl-ammonium chloride (14, L-cysteine choline ester chloride). To a solution of 12 (1.3 g, 1.93 mmol) in CH$_2$Cl$_2$ (20 ml) was added to Et$_3$SiH (2.28 ml, 14.3 mmol) and anhydrous CF$_3$COOH (6 ml) subsequently. The mixtures were stirred at room temperature for 1 h. The solution was dried under reduced pressure. The residue was dissolved into Et$_2$O (25 ml) and 1% HCl aqueous solution (25 ml). The aqueous solution was separated, rinsed twice with Et$_2$O (5 ml×2), neutralized by 10% NaHCO$_3$ to pH 7.0, and then lyophilized. The residue was purified by a preparative reversed-phase C18 column (20 cm×2.5 cm) with 5% CH$_3$CN in H$_2$O as eluent to give products 14 as a chloride salt (398 mg, 85%); $^1$H NMR (D$_2$O/CD$_3$OD, 400 MHz): 4.76 (br, 1H), 4.51 (t, 2H, J=5.00 Hz), 3.83 (t, 2H, J=4.91 Hz), 3.24 (s, 9H), 3.17 (d, 2H, J=4.58 Hz); $^{13}$C NMR (CDCl$_3$, 100 MHz): 168.3, 65.3, 61.1, 55.4, 54.7, 24.7; Electrospray-ion trap-MS: Calcd for $C_8H_{19}N_2O_2S^+$: m/z 207.1. Found: m/z 207.0 [M]$^+$.

FIG. 1 also shows a preferred method for the synthesis of (R)-[2-(2,2-Dimethyl-thiazolidine-4-carbonyloxy)-ethyl]triethyl-ammonium chloride.

(R)-[2-(2,2-Dimethyl-thiazolidine-4-carbonyloxy)-ethyl]-trimethyl-ammonium chloride (15): Compound 14 (150 mg, 0.62 mmol) was dissolved into 10 ml acetone. After 20 minutes, the precipitate was filtered and rinsed with acetone (5 ml×2) to give 15 as a white solid (161 mg, 92%); $^1$H NMR (D$_2$O/CD$_3$OD, 400 MHz): 5.15 (t, 1H, J=8.31 Hz), 3.87 (m, 2H), 3.85 (m, 1H), 3.76 (dd, 1H, J=8.25 & 12.0 Hz), 3.64 (dd, 1H, J=8.31 & 12.0 Hz), 3.26 (s, 9H), 3.21 (dd, 1H, J=5.10 & 12.0 Hz), 1.86 (s, 3H), 1.84 (s, 3H). $^{13}$C NMR (D$_2$O/CD$_3$OD, 100 MHz): 167.4, 73.9, 65.3, 62.5, 61.4, 54.8, 32.2, 28.9, 27.6; Electrospray-ion trap-MS: Calcd for $C_{11}H_{23}N_2O_2S^+$: m/z 247.1. Found: m/z 247.1 [M]$^+$.

Example 2

Synthesis of Glutathione Choline Ester

All reactions were carried out under dry N$_2$ except where noted. All solvents were distilled from drying agents. Reagents were purchased from Aldrich and VWR. Normal phase column chromatography was performed on Silica Gel 60 (230-400 Mesh, EM Science). Reverse phase column chromatography was performed on Bakerbond™ C$_{18}$ (40 μm, J. T. Baker). $^1$H, $^{13}$C, and COSY NMR data were recorded on a Bruker Avance 400 with Me$_4$Si as the internal standard except where noted. MS analyses were performed with an Agilent LC/MSD ion-trap mass spectrometer (Agilent Technologies) with an electrospray interface operated in the positive-ion mode.

Figure 2:
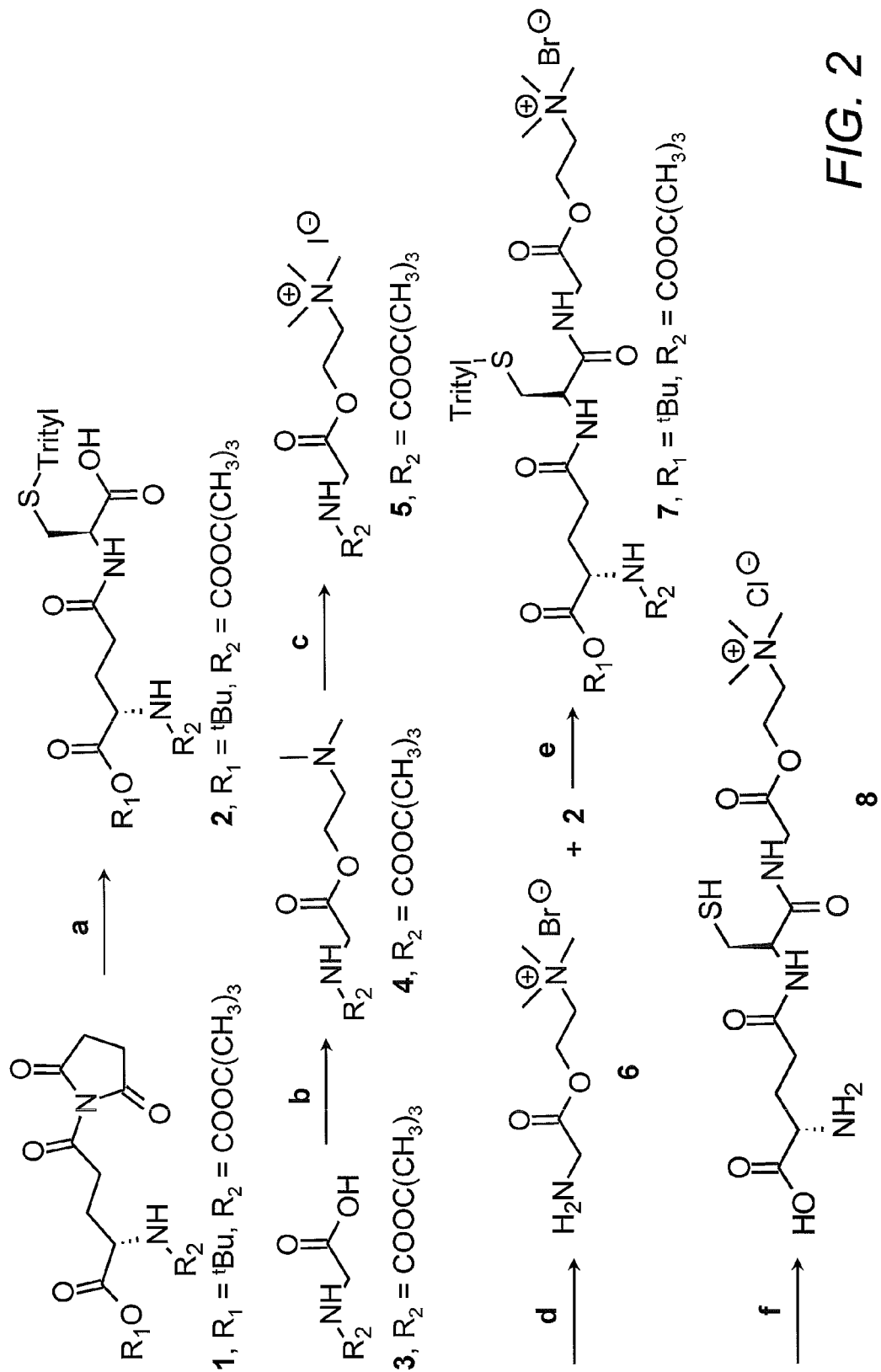
FIG. 2 shows a method for the synthesis of glutathione choline ester. a: to 1 in DMF was added S-trityl-L-cysteine and triethylamine with stirring at room temperature for 12 hours. b: to 3, DCC, and triethylamine in $CH_2Cl_2$ was added 2-(dimethylamino)-ethanol with stirring at room temperature for 12 hours. c: to 4 in THF was added methyl iodide with stirring for 12 hours at room temperature. d: HBr in glacial acetic acid with stirring for 30 minutes at room temperature. e: to 2, HOBt, and DIC in $CH_2Cl_2$ was added 6 and triethylamine in DMF with stirring for 24 hours. f: 7 in $CH_2Cl_2$ was added to $Et_3SiH$ and anhydrous $CF_3COOH$ with stirring at room temperature for 3 hours.

FIG. 2 shows a preferred approach for the synthesis of glutathione choline ester. The α-carboxylic acid and amino groups of glutamic acid were protected by forming tert-butyl ($^t$Bu) ester and tert-butyl carbamate respectively. The thiol group of cysteine was protected as a trityl thioether. The key step in the synthesis was coupling of the protected L-γ-glutamyl-L-cysteine (Marsh et al., "Solid Phase Synthesis of Polyamine Conjugates for the Study of Trypanothione Reductase," Tetrahedron 53:17317-17334 (1997), which is hereby incorporated by reference in its entirety), and glycine choline ester (Mndzhoyan et al., "Synthesis of the choline ester glycine," Khimiko-Farmatsevticheskii Zhurnal 14:34-36 (1980), which is hereby incorporated by reference in its entirety) to afford glutathione choline ester catalyzed by diisopropylcarbodiimide (DIC) (Flohr et al., "Chemoenzymic Synthesis of Nucleopeptides," Chemistry 5:669-681 (1999), which is hereby incorporated by reference in its entirety). Simultaneous deprotection of $^t$Bu, tert-butyloxycarbonyl, and trityl groups were accomplished by trifluoroacetic acid with a carbocation scavenger triethylsilane.

Boc-L-glutamyl-α-O-tert-butyl-τ-(S-trityl-L-cysteine) (2): To a solution of boc-L-glutamyl-α-tert-butyl-N-oxosuccinimide ester (Henderson et al., "Synthesis and NMR Characterization of the Trypanosomatid Metabolite, N1,N8-bis (glutathionyl)spermidine disulphide (trypanothione disulphide)," J. Chem. Soc. Perkin Trans 1:911-914 (1999), which is hereby incorporated by reference in its entirety) (1.04 g, 2.6 mmol) in DMF (10 ml) was added S-trityl-L-cysteine (554 mg, 2.6 mmol) and triethylamine (0.362 ml, 2.5 mmol). The mixtures were stirred at room temperature for 12 h. The resulting mixture was added 20 ml 5% citric acid and extracted with ethyl acetate (20 ml×3). The organic extract was rinsed with water (20 ml×2) and brine (20 ml×2) and dried with anhydrous MgSO$_4$. The dried EtOAc extract was filtered and filtrate was evaporated to give a crude residue. The residue was purified by chromatography on silica gel (ethyl acetate/hexane 1:1) to give 2 as a white solid (1.36 g, 81%); $^1$H NMR (Acetone-d$_6$, 400 MHz): 7.42-7.22 (m, 15H), 6.30 (d, 1H, J=8 Hz, NH), 4.43 (dd, 1H, J=7.16 & 12.5 Hz), 4.05 (m, 1H), 2.68 (dd, 1H, J=7.49 & 12.2 Hz), 2.60 (dd, 1H, J=5 & 12.2 Hz), 2.37 (t, 2H, J=7.41 Hz), 2.08 (m, 1H), 1.92 (m, 1H), 1.43 (s, 9H), 1.40 (s, 9H); $^{13}$C NMR (Acetone-d$_6$, 100 MHz): 172.6, 172.3, 172.0, 156.4, 145.4, 130.2, 128.7, 127.6, 81.4, 79.1, 67.2, 54.9, 52.1, 49.7, 34.4, 32.6, 28.5, 28.1; Electrospray-ion trap-MS: Calcd for $C_{36}H_{44}N_2O_7S$: m/z 648.3. Found: m/z 671.1 [M+Na]$^+$.

Boc-glycine-2-(dimethylamino)ethyl ester (4): To a solution of boc-glycine (1.0 g, 5.7 mmol), DCC (1.82 g, 8.84 mmol), and triethylamine (0.84 ml, 6.05 mmol) in CH$_2$Cl$_2$ at 0° C. was added 2-(dimethylamino)-ethanol (1.5 ml, 14.6 mmol). The mixtures were allowed to warm to room temperature. After stirring for 12 h, the solution was filtered, extracted with 1% HCl, saturated NaHCO$_3$, water, and brine subsequently. The extracted CH$_2$Cl$_2$ solution was dried with anhydrous MgSO$_4$ and evaporated to dryness. The white residue was purified by chromatography on silica gel (ethyl acetate/methanol 9:1) to give 4 (1.03 g, 74%) as a white solid; $^1$H NMR (C$_6$D$_6$, 400 MHz): 5.51 (t, 1H, J=5.90 Hz, NH), 4.01 (t, 2H, J=5.88 Hz), 3.75 (d, 2H, J=5.90 Hz), 2.22 (t, 2H, J=5.88 Hz), 1.98 (s, 6H), 1.40 (s, 9H); $^{13}$C NMR (C$_6$D$_6$, 100 MHz): 170.4, 156.0, 79.1, 62.8, 57.7, 45.4, 42.7, 28.4; Electrospray-ion trap-MS: Calcd for $C_{11}H_{22}N_2O_4^+$: m/z 246.2. Found: m/Z 247.0 [M+H]$^+$.

Boc-glycine choline ester iodide (5): To a solution of boc-glycine-2-(dimethylamino)ethyl ester (1.2 g, 4.88 mmol) in THF at 0° C. was added methyl-iodide (1.5 ml, 24.4 mmol). The solution was stirred for 12 h at room temperature. The formed white precipitate was filtered to give 5 (1.76 g, 93%) as a white solid; $^1$H NMR (CD$_3$OD, 400 MHz): 4.04 (b, 2H), 3.92 (s, 2H), 3.30 (b, 2H), 2.75 (s, 9H), 0.83 (s, 9H); $^{13}$C NMR (CD$_3$OD, 100 MHz): 171.4, 158.2, 80.8, 66.0, 59.8, 55.0, 43.5, 28.9; Electrospray-ion trap-MS: Calcd for $C_{12}H_{25}N_2O_4^+$: m/z 261.2. Found: m/z 261.0 [M]$^+$.

Glycine choline ester bromide (6). A solution of boc-glycine choline ester iodide (1.76 g, 4.5 mmol) in HBr in glacial acetic acid (30%, 8 ml) was stirred for 30 min at room temperature. After addition of ice-cold Et$_2$O (100 ml), the brown precipitate was filtered to give 6 as a yellowish solid; $^1$H NMR (CD$_3$OD/D$_2$O, 400 MHz): 4.13 (t, 2H, J=4.63 Hz), 3.40 (s, 2H), 3.28 (t, 2H, J=4.63 Hz), 2.68 (s, 9H); $^{13}$C NMR (CD$_3$OD/D$_2$O, 100 MHz): 167.9, 65.7, 60.6, 54.9, 41.4; Electrospray-ion trap-MS: Calcd for free base $C_7H_{17}N_2O_2^+$: m/z 161.1. Found: m/z 161.0 [M]$^+$.

N-Boc-α-O-tert-butyl-τ-(S-trityl)-glutathione choline ester bromide (7): A solution of 2 (1.43 g, 2.2 mmol), HOBt (311 mg, 2.3 mmol), and DIC (438 µl, 2.3 mmol) in CH$_2$Cl$_2$ (30 ml) was stirred for 30 min and then added a solution of give glycine choline ester bromide (0.7 g, 2.2 mmol) and triethylamine (0.322 ml, 2.3 mmol) in DMF (20 ml). After 24 h, the brown solution was concentrated by evaporating CH$_2$Cl$_2$ under reduced pressure. The yellowish product was precipitated by addition of ice-cold Et$_2$O (50 ml). The solution was decanted and the precipitate was rinsed with Et$_2$O (10 ml×2). The precipitate was re-dissolved into CH$_3$CN and re-crystallized in Et$_2$O to yield 7 (1.2 g, 64%) as a yellowish solid; $^1$H NMR (Acetone-d$_6$, 400 MHz): 7.42-7.22 (m, 15H), 4.58 (br, 2H), 4.38 (br, 1H), 3.99 (br, 2H), 3.97 (br, 1H), 3.89 (br, 2H), 3.40 (s, 9H), 2.75(m, 1H), 2.57 (m, 1H), 2.43 (m, 2H), 2.08 (m, 1H), 1.98 (m, 1H), 1.41 (s, 9H), 1.38 (s, 9H); $^{13}$C NMR (Acetone-d$_6$, 100 MHz): 172.7, 172.2, 171.4, 169.4, 156.2, 145.1, 129.9, 128.4, 127.1, 80.9, 78.7, 78.6, 66.8, 65.6, 64.8, 59.0, 54.8, 54.0, 53.1, 41.6, 34.4, 28.2, 27.7; Electrospray-ion trap-MS: Calcd for $C_{43}H_{59}N_4O_8S^+$: m/z 791.4. Found: m/z 791.0 [M]$^+$.

Glutathione choline ester chloride (8): To a solution of 7 (766 mg, 0.88 mmol) in CH$_2$Cl$_2$ (15 ml) was added to Et$_3$SiH (1.1 ml, 6.9 mmol) and anhydrous CF$_3$COOH (8 ml) subsequently. The mixtures were stirred at room temperature for approximately 3 h till color of solution did not change. The solution was dried under reduced pressure. The oily residue was dissolved into Et$_2$O (15 ml) and 1% HCl aqueous solution (15 ml). The aqueous solution was separated, rinsed twice with Et$_2$O (5 ml), neutralized by 10% NaHCO$_3$ to pH 7.5, and then lyophilized to give the yellowish crude residue. The residue was purified by a preparative reversed-phase. C18 column (20 cm×2.5 cm) with 1% CH$_3$CN in H$_2$O as eluent to give 8 (328 mg, 87%); $^1$H NMR (CD$_3$OD/D$_2$O, 400 MHz): 4.63 (t, 2H, J=4.64 Hz), 4.55 (t, 1H, J=6.08 Hz), 4.09 (s, 2H), 3.88 (t, 1H, 6.40 Hz), 3.76 (t, 2H, J=4.64 Hz), 3.20 (s, 9H), 2.93 (m, 2H), 2.56 (m, 2H), 2.18 (m, 2H); $^{13}$C NMR (CD$_3$OD/D$_2$O, 100 MHz): 175.7, 174.6, 173.6, 171.1, 65.3, 60.0, 56.5, 54.7, 42.2, 32.1, 32.0, 27.0, 26.3; Electrospray-ion trap-MS: Calcd for $C_{15}H_{29}N_4O_6S^+$: m/z 393.2. Found: m/z 393.2 [M]$^+$.

Example 3

Oxidative Stress Induces Apoptosis of Spinal Cord Neurons

Figure 3A:
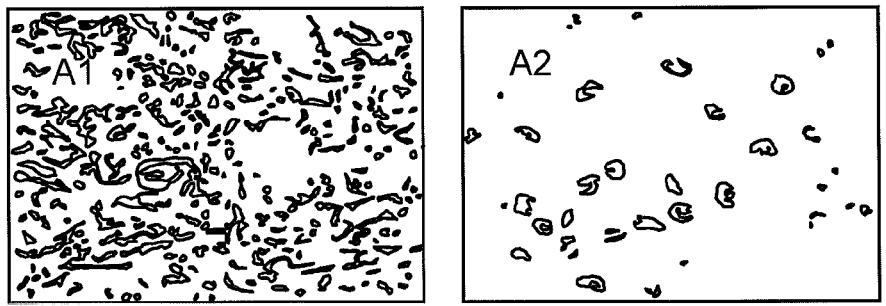
FIGS. 3A-E demonstrate that oxidative stress induces nuclear condensation and fragmentation of nuclei in spinal cord neurons. Using phase contrast and Hoechst staining of image pairs.
Figure 3B:
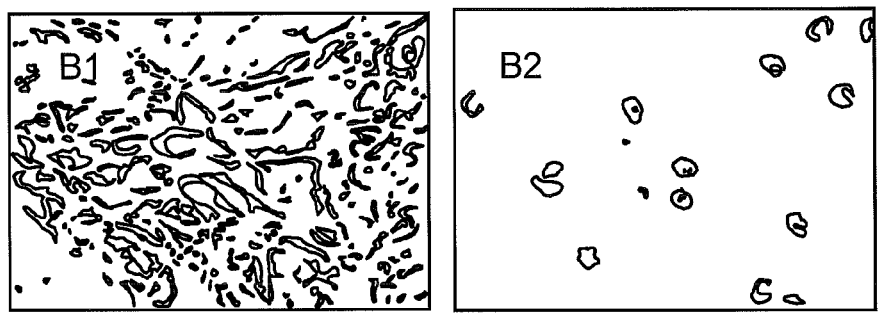
Figure 3C:
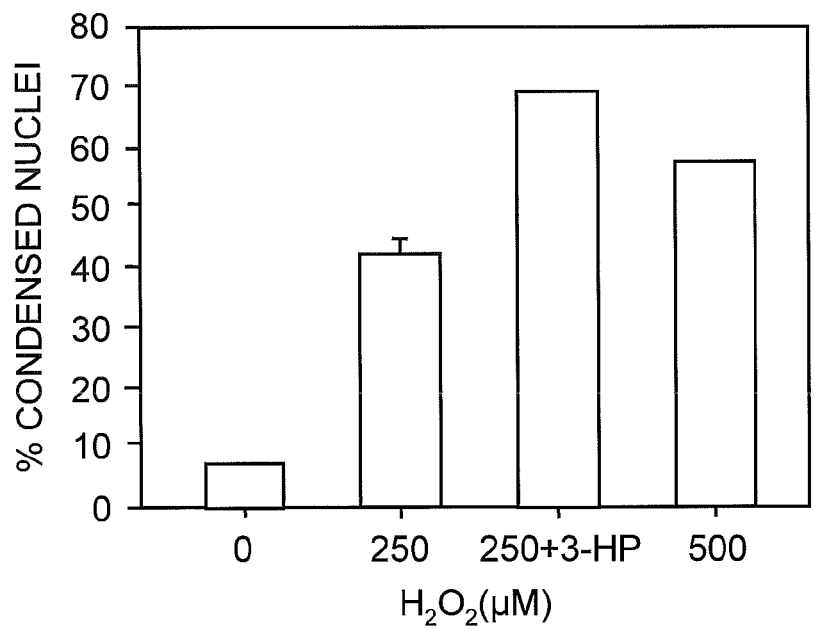
Figure 3D:
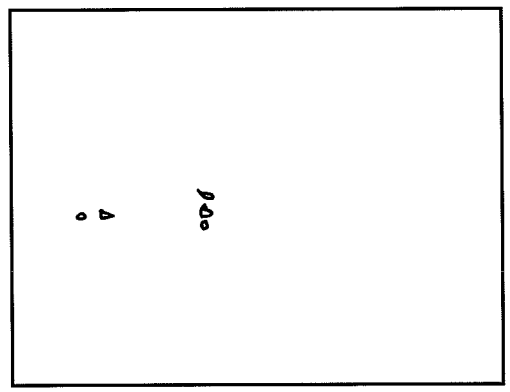
Figure 3E:
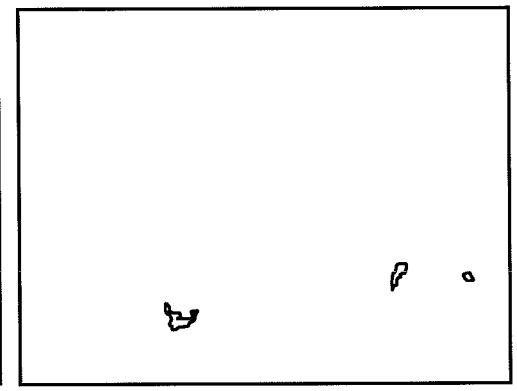

Central to the proposed therapeutic intervention is the belief that SCN undergo apoptosis and possibly necrosis under oxidative stress. Data in FIGS. 3A-E demonstrate that H$_2$O$_2$-induced changes are indicative of neuronal apoptosis in cultured SCN model system. Image pairs, obtained from H$_2$O$_2$-treated (FIG. 3A) and non-treated (FIG. 3B) SCN, are shown in both phase contrast and after Hoechst nuclear staining. Many of the neurons in FIG. 3A show condensed and fragmented nuclei (arrows) indicative of apoptotic cells. In contrast, control neurons in FIG. 3B show predominantly diffuse nuclear staining (arrows). Quantification of these data (FIG. 3C) demonstrates a significant increase in the number of neurons with condensed and fragmented nuclei after H$_2$O$_2$ treatment. At 250 µM H$_2$O$_2$, ~42% of neurons exhibited condensed and fragmented nuclei. This percentage increased to ~58% for 500 µM H$_2$O$_2$. Selective depletion of mtGSH by 3-hydroxy-4-pentenoate (3-HP) (Shan et al., "Selective Depletion of Mitochondrial Glutathione Concentrations by (R,S)-3-hydroxyl-4-pentenoate Potentiates Oxidative Cell Death." Chem. Res. Toxicol, 6:75-81 (1993); Hashmi et al., "Enantioselective Depletion of Mitochondrial Glutathione Concentrations by (S)- and (R)-3-hydroxy-4-pentenoate," Chem. Res. Toxicol. 9:361-364 (1996), each of which is hereby incorporated by reference in its entirety), prior to 250 µM H$_2$O$_2$ treatment increased percentage of cells showing these changes to 70%. These changes were concentration-dependent and increased by mtGSH depletion. Immunohistochemical staining for Cyt C shows punctate immunoreactivity in control neurons and a loss of this discrete localization in apoptotic cells, suggesting that H$_2$O$_2$ induces Cyt C release (FIG. 3D). In contrast, immunoreactivity to cytochrome C oxidase (COX), a marker in the inner mitochondrial membrane remains independent of the mitochondrial insults by H$_2$O$_2$ (FIG. 3E). The differential staining between Cyt C and COX affords a secondary method to assess whether a given neuron has undergone mitochondrial permeability transition (MPT).

Example 4

H$_2$O$_2$ Induces Mitochondrial Permeability Transition

Figure 4A:
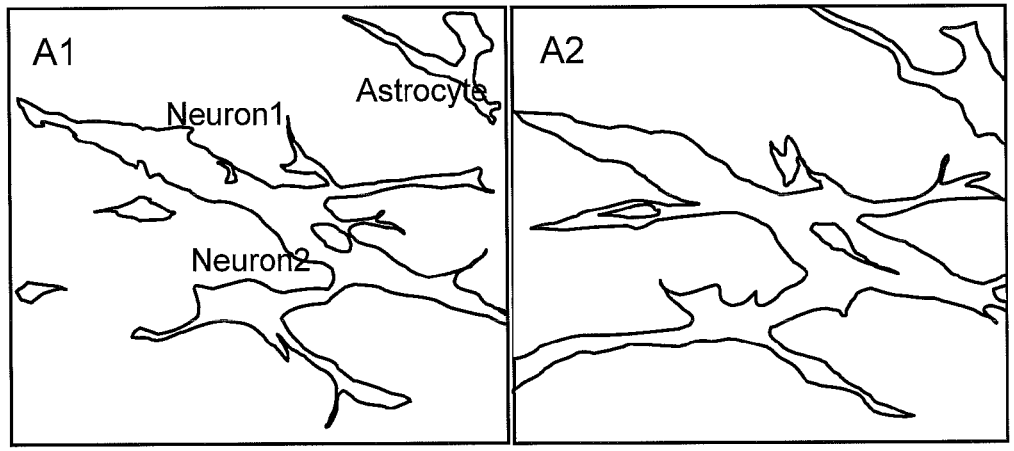
FIGS. 4A-D demonstrate that oxidative stress induces a loss of mitochondrial membrane potential.
Figure 4B:
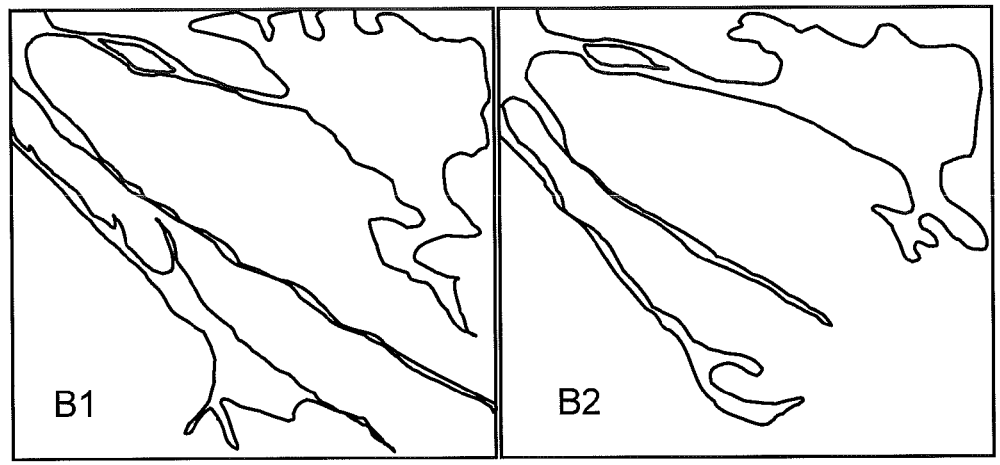
Figure 4C:
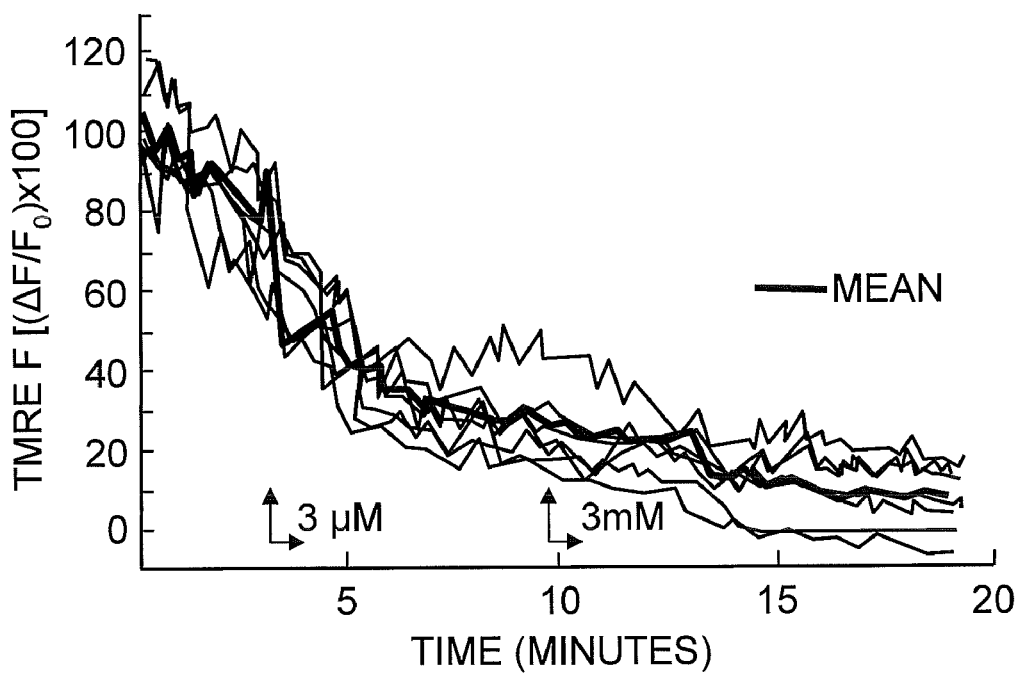
Figure 4D:
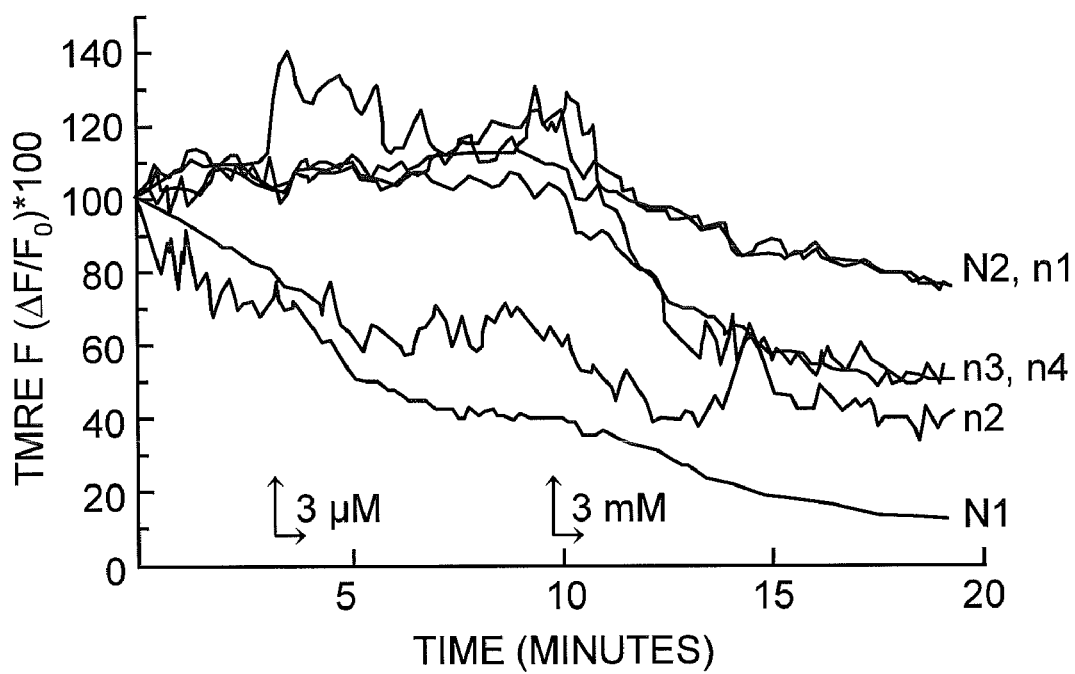

FIG. 4B shows H$_2$O$_2$-induced time-dependent loss of mitochondrial TMRE fluorescence indicative of dissipated ΔΨ$_m$. This loss of punctate or filamentous fluorescence by H$_2$O$_2$ is not due to photobleaching because the control experiment, done without H$_2$O$_2$, shows that the punctuate pattern after 20 minutes of recording is still preserved (FIG. 4A). Cyclosporin A (CsA) inhibits the effect of H$_2$O$_2$, supporting the conclusion that loss of TMRE fluorescence is indeed a measure of MPT. Further quantitative analysis of the images revealed two interesting observations. First, mitochondria within a given neuronal soma behave similarly (FIG. 4C). Second, significant heterogeneity in the timing of MPT exists depending on the sub cellular location of the mitochondria within a neuron (e.g. soma vs. neurites) (FIG. 4D). This differential susceptibility of mitochondria is a novel observation to be explored.

Example 5

Assessment of Neuronal Glutathione Level by Monochlorobimane (MCIB)

Figure 5A:
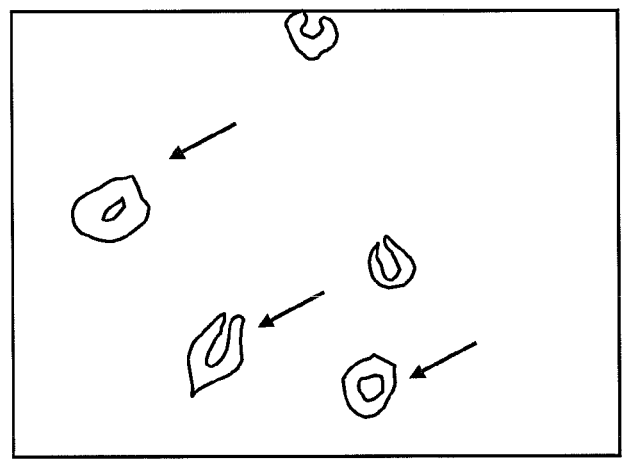
FIGS. 5A-C demonstrate the heterogeneity of cellular GSH in spinal cord neurons. Cells were labeled with MCIB (50 μg/ml) and imaged under fluorescence microscopy. A phase contrast and fluorescent image pair of the same field are shown in FIGS. 5A and 5B, respectively. The intense MCIB fluorescence indicates of high cellular GSH levels in phase bright neurons (dark arrows) in contrast to the large multipolar neuron with minimal MCIB signal (white arrow).
Figure 5B:
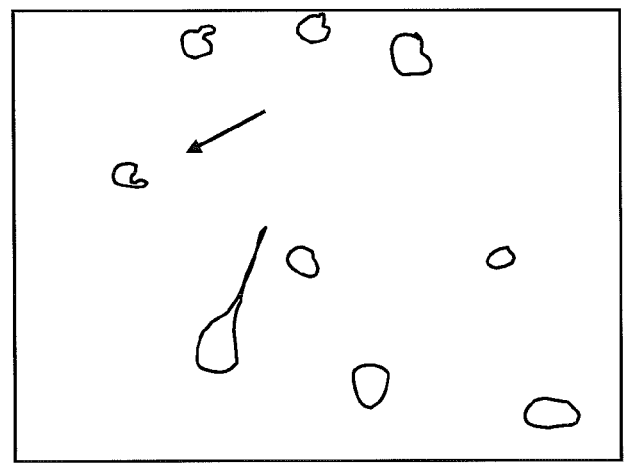
Figure 5C:
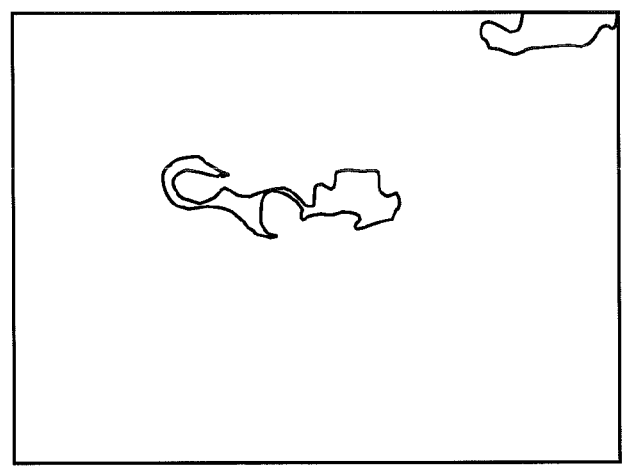

Cellular and subcellular GSH can be determined with fluorescence microscopy using the GSH-reactive fluorescent probe MCIB. This reporter is non-fluorescent in its native state but turns fluorescent when reacted with GSH; the final conjugate exhibiting excitation in the UV range (ex. 385 nm, em 485 nm). This reporter has been used to determine cellular GSH levels (Fricker et al., "Measurement of Glutathione Levels in Intact Roots of Arabidopsis," J. Microscopy 198: 162-173 (2000); Tauskela et al., "Evaluation of Glutathione-sensitive Fluorescent Dyes in Cortical Culture," Glia 30:329-341 (2000), each of which is hereby incorporated by reference in its entirety). FIGS. 5A-C show MCIB staining of SCN. Both phase bright neuronal and flat background glia cells are fluorescent indicating presence of GSH in both cell types. Semi-permeabilization of the neuronal membrane with saponin releases cellular MCIB-GSH conjugate leaving the mitochondrial fluorescence intact (FIG. 5C). This allows assessment of mitochondrial GSH in neurons in situ, without resorting to the biochemical isolation of mitochondria and a subsequent HPLC analysis of GSH content. Of note is the heterogeneity in MCIB fluorescence between neurons. The phase bright, small, bipolar neurons exhibit bright fluorescence, whereas, the large multipolar neuron (arrow in FIGS. 5A-B) is only weakly fluorescent. Differences in neuronal GSH levels may underlie the differential vulnerability of neuronal populations in the spinal cord. This observation is consistent with the implication that the large multipolar neurons are more likely to die under oxidative stress as has been suggested for the greater susceptibility of motoneurons to excitotoxic insults (Urushitani et al., "Neuroprotective Effect of Cyclic GMP Against Radical-induced Toxicity in Cultured Spinal Motor Neurons," *J. Neurosci. Res.* 61:443-448 (2000); Carriedo et al., "AMPA Exposures Induce Mitochondrial $Ca^{(2+)}$ Overload and ROS Generation in Spinal Motor Neurons in vitro," *J. Neurosci.* 20:240-250 (2000), each of which is hereby incorporated by reference in its entirety). A systematic correlation between neuronal morphology (aided by motorneuron specific markers) and GSH level will attest to this hypothesis. A similar heterogeneity in MC1B fluorescence (and hence cellular GSH levels) among glia cells has been reported previously (Chatterjee et al., "Glutathione Levels in Primary Glial Cultures: Monochlorobimane Provides Evidence of Cell Type-Specific Distribution," *Glia* 27:152-161 (1999), which is hereby incorporated by reference in its entirety).

Example 6

Inhibition of Reactive Oxygen Species In Vitro

Figure 6:
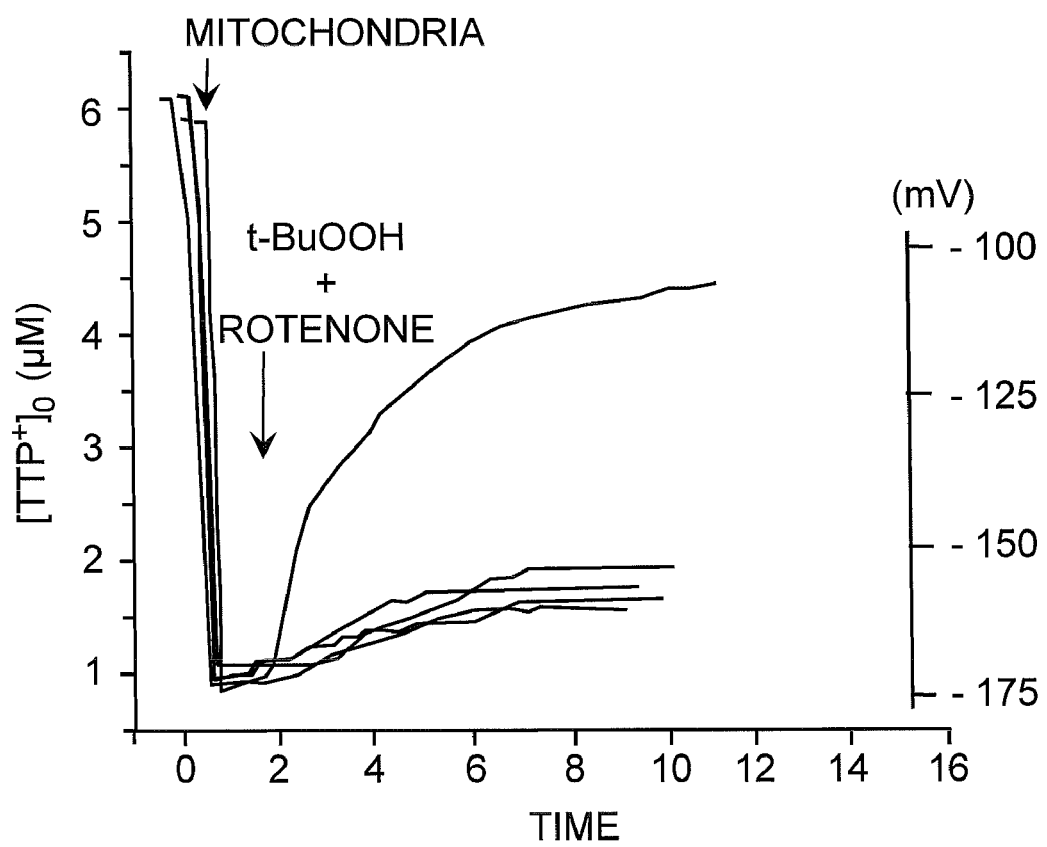
FIG. 6 demonstrates the ability of cysteine choline ester, N-acetyl cysteine choline ester, glutathione choline ester (Mito GSH), and S,N-acetyl-L-cysteine choline ester to prevent the depolarization of membrane potential in isolated heart mitochondria induced by rotenone- and tert-butylhydroperoxide (t-BuOOH)-induced oxidative stress. The scale on the right side of the graph shows changes in mV in the mitochondrial membrane potential.

The ability of cysteine choline ester, N-acetyl cysteine choline ester, mitochondrial-targeted glutathione choline ester (Mito GSH), and mitochondrial-targeted N-acetyl-L-cysteine choline ester to prevent the depolarization of mitochondrial membrane potential induced by oxidative stress was assessed. Mitochondrial membrane potential was measured by a TPP+ (tetraphenyl phosphonium) sensitive electrode. Rat heart mitochondria (1 mg protein/100 µl) were transferred to a beaker (at the first arrow) containing 0.9 ml of 150 mM KCl, 5 mM Hepes, 6 µM TPP+ and 5 mM succinate buffer. As shown in FIG. 6, this caused a downward shift in the TPP+ signal due to a decrease in TPP+ concentration in the extramitochondrial solution as the probe was taken up by mitochondria. At the second arrow, mitochondria were subjected to oxidative stress by adding 5 µM rotenone (Complex I inhibitor) and 100 µM tert-butylhydroperoxide (t-BuOOH) to the buffer. This led to mitochondrial depolarization, resulting in release of intramitochondrial TPP+ as seen by an increase in TPP+ signal. Pretreatment of mitochondria with anti-oxidants (5 mM at 4° C. for 30 minutes, then resuspended mitochondria in drug free solution), prevented the oxidative stress-induced depolarization significantly (FIG. 6). The scale on the right side of the graph shows changes in mV in the mitochondrial membrane potential.

Example 7

Figure 7:
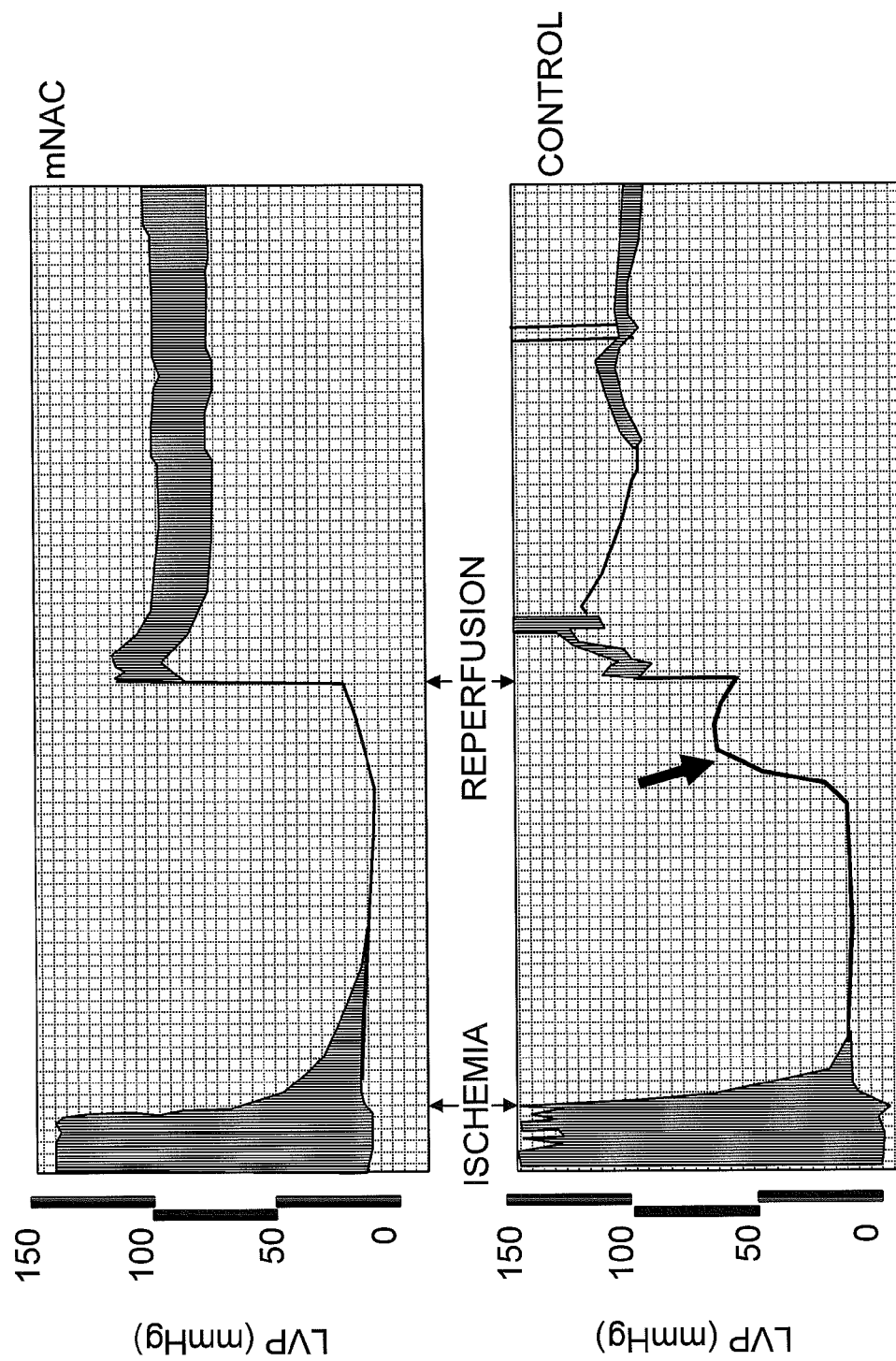
FIG. 7 demonstrates that N-acetyl-L-cysteine choline ester (mNAC) improves post-ischemic recovery in rat heart. Male Sprague-Dawley rat hearts were retrograde (Langendorff) perfused with oxygenated Krebs Henseleit (KH) buffer in constant flow mode (12 mL/min/gram wet weight). Hearts were not electrically stimulated, and beat spontaneously at approximately 280 bpm. Left-ventricular pressure (LVP) was measured by a balloon inserted in the left ventricle, linked to a pressure transducer with digital recording at 500 Hz. Traces are shown with the X-axis (time) compressed. Following an equilibration period of approximately 25 mm., global normothermic ischemia was imposed for 25 mm., followed by reperfusion for 30 mm as indicated by the arrows on the traces. For mNAC treatment, the drug was dissolved in KH buffer and infused via a port just above the aortic perfusion cannula, at a final concentration of 50 µM, for 10 min. prior to the onset of ischemia. Overall recovery of LV developed pressure (systolic minus diastolic) was 4.1% for control, and 15.7% for mNAC treated. It is also apparent that mNAC appeared to delay the onset of ischemic contracture (open arrow).

Mitochondrially Targeted N-Acetyl-L-Cysteine (mNAC) Improves Post-Ischemic Recovery in Rat Heart The ability of mitochondrially targeted N-acetylcysteine (mNAC) to improve post-ischemic recovery in rat heart was assessed. Male Sprague-Dawley rat hearts were retrograde (Langendorff) perfused with oxygenated Krebs Henseleit (KH) buffer in constant flow mode (12 mL/min/gram wet weight). Hearts were not electrically stimulated, and beat spontaneously at approximately 280 beats per minute. Left-ventricular pressure (LVP) was measured by a balloon inserted in the left ventricle, linked to a pressure transducer with digital recording at 500 Hz. The results of this experiment are shown in FIG. 7. Traces are shown with the X-axis (time) compressed. Following an equilibration period of approximately 25 min., global normothermic ischemia was imposed for 25 min., followed by reperfusion for 30 min as indicated by the arrows on the traces. For mNAC treatment, the drug was dissolved in KH buffer and infused via a port just above the aortic perfusion cannula, at a final concentration of 50 µM, for 10 min. prior to the onset of ischemia.

As shown in FIG. 7, overall recovery of LV developed pressure (systolic minus diastolic) was 4.1% for control, and 15.7% for mNAC treated. It is also apparent that mNAC appeared to delay the onset of ischemic contracture (open arrow).

Example 8

Figure 8:
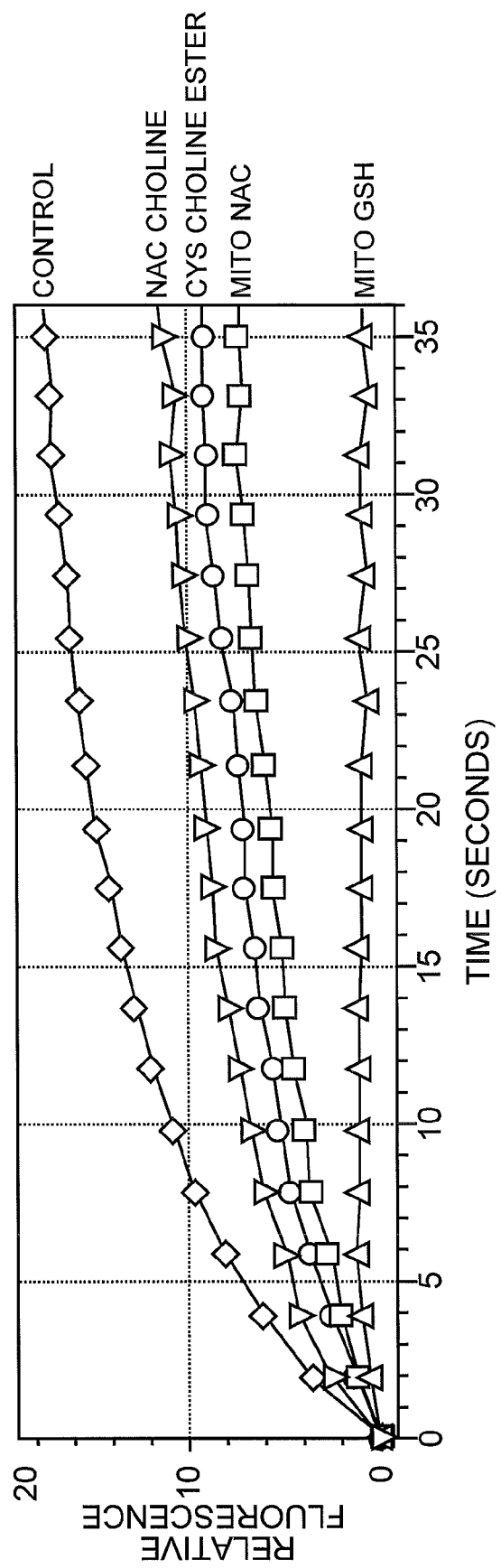
FIG. 8 demonstrates the ability of cysteine choline ester, N-acetyl cysteine choline ester, glutathione choline ester (Mito GSH), and S,N-acetyl-L-cysteine choline ester (Mito NAC) to minimize the depolarization of mitochondrial membrane potential induced by oxidative stress.

Mitochondrial-targeted Antioxidants Prevent the Depolarization of Mitochondrial Membrane Potential Induced by Oxidative Stress The ability of cysteine choline ester, N-acetyl cysteine choline ester, glutathione choline ester (Mito GSH), and N-acetyl-L-cysteine choline ester (Mito NAC) to prevent the depolarization of mitochondrial membrane potential induced by oxidative stress was assessed (FIG. 8). Mitochondrial membrane potential was measured by safranine. Safranine is a positively charged dye that accumulates in mitochondria on establishment of an electrical potential across the mitochondrial inner membrane. However, its fluorescence is quenched by its accumulation in mitochondria in response to mitochondrial membrane potential. Rat heart mitochondria (0.2 mg protein/200 µl) were transferred to a well containing 0.3 ml of 150 mM KCl, 5 mM Hepes, 15 µM safranine, 5 mM succinate buffer, 5 µM rotenone and 100 µM t-BuOOH. The mitochondria were placed in a multiplate reader. Fluorescence measurements were made with excitation and emission wavelengths of 485 and 585 nm respectively. Rotenone and t-BuOOH induced mitochondrial membrane potential resulting in a release of intramitochondrial safranine indicated by an increase in fluorescence signal. Pretreatment of mitochondria with mitochondrial-targeted antioxidants, glutathione choline ester (Mito GSH), N-acetyl cysteine choline ester, N,S-acetyl cysteine choline ester (Mito NAC), and CYS-choline ester (5 mM for 30 minutes and then resuspended in a drug free solution) diminished the release of intramitochondrial safaranine, indicating a protective effect of these compounds.

Example 9

Figure 9:
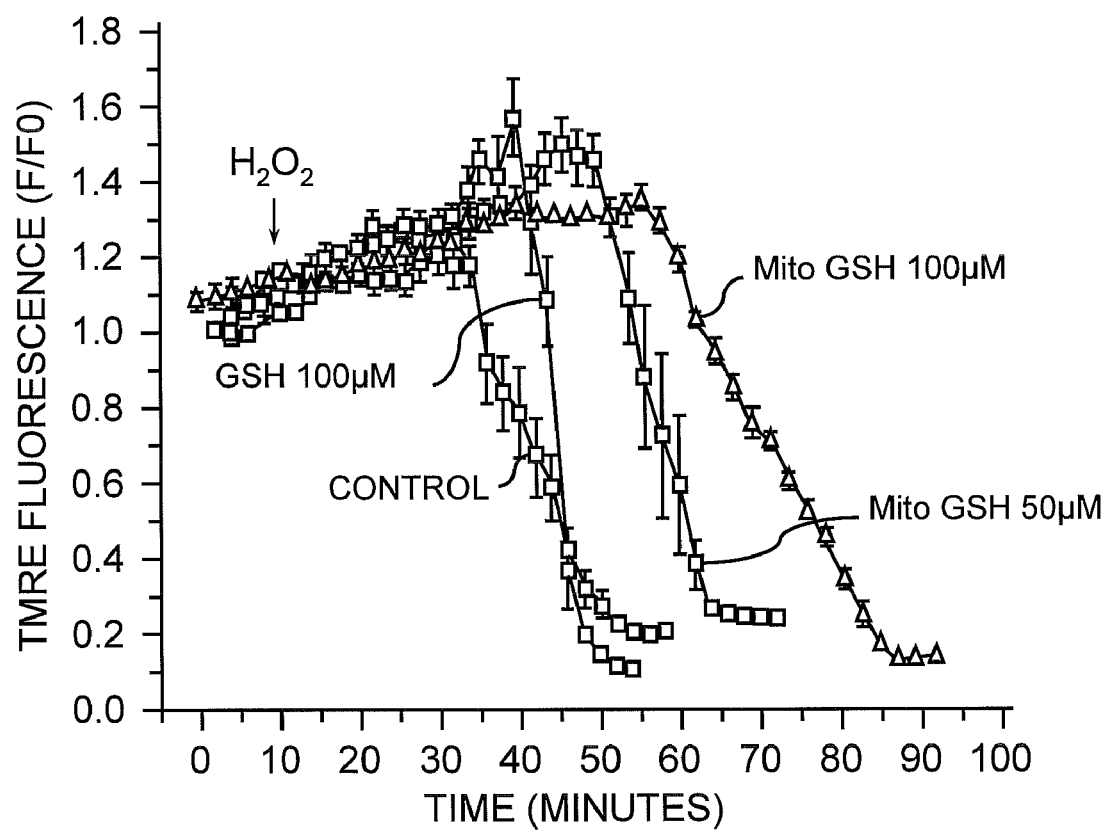
FIG. 9 demonstrates the ability of glutathione choline ester (Mito GSH) to delay the onset of $H_2O_2$-induced depolarization of mitochondrial membrane potential in cultured neonatal rat ventricular myocytes.

Mitochondrial-targeted Antioxidant Glutathione Choline Ester (Mito GSH) Delays the Onset of Oxidative Induced Depolarization of Mitochondrial Membrane Potential Using tetramethylrhodamine methyl ester (TMRM) as an indicator of mitochondrial membrane potential, the ability of mitochondrial-targeted glutathione choline ester (Mito GSH) to delay the onset of $H_2O_2$-induced depolarization of mitochondria membranes was assessed (FIG. 9). TMRM is a lipophilic cation that partitions selectively into the negatively charged mitochondria Neonatal cultured myocytes (6 days in culture) were loaded with 10 nM TMRM for 60 minutes at 37° C. The myocytes were pretreated with either 50 or 100 µM Mito GSH or 100 µM non-targeted GSH for 30 minutes and then washed to remove the antioxidants from the solution in which myocytes were suspended. As a control, myocytes were not pretreated with any drug. TMRM was excited at 555 nm and fluorescence emission was detected at 590 nm. Fluorescence images were taken every 2 minutes. At the arrow, myocytes were subjected to oxidative stress by adding 50 µM $H_2O_2$. Plots were normalized to baseline, and are shown as F/Fo, where F is the emitted fluorescence at any given time and Fo is the baseline fluorescence before addition of $H_2O_2$. Mito GSH pretreatment delayed onset of $H_2O_2$-induced depolarization and loss of TMRM fluorescence. The traces were drawn from the mean values of 7-10 experiments.

Figure 10A:
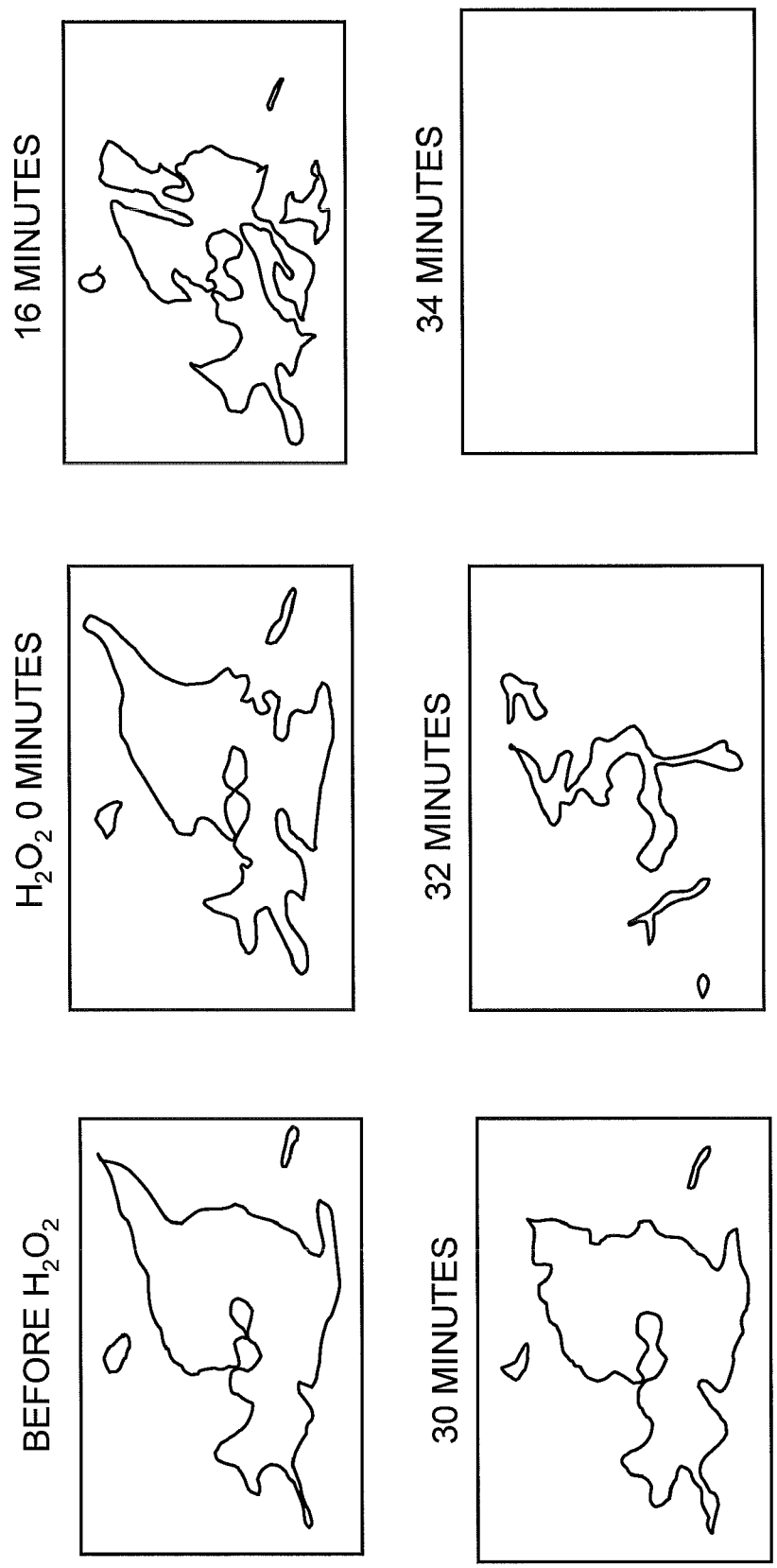
FIGS. 10A-B shows time-lapse traces of tetramethylrhodamine methyl ester (TMRE) fluorescence from cardiac myocytes after $H_2O_2$ treatment in control (FIG. 10A) and glutathione choline ester (Mito GSH) (FIG. 10B) pre-treated cells, demonstrating the protective effect of pre-treatment of cells with Mito GSH.
Figure 10B:
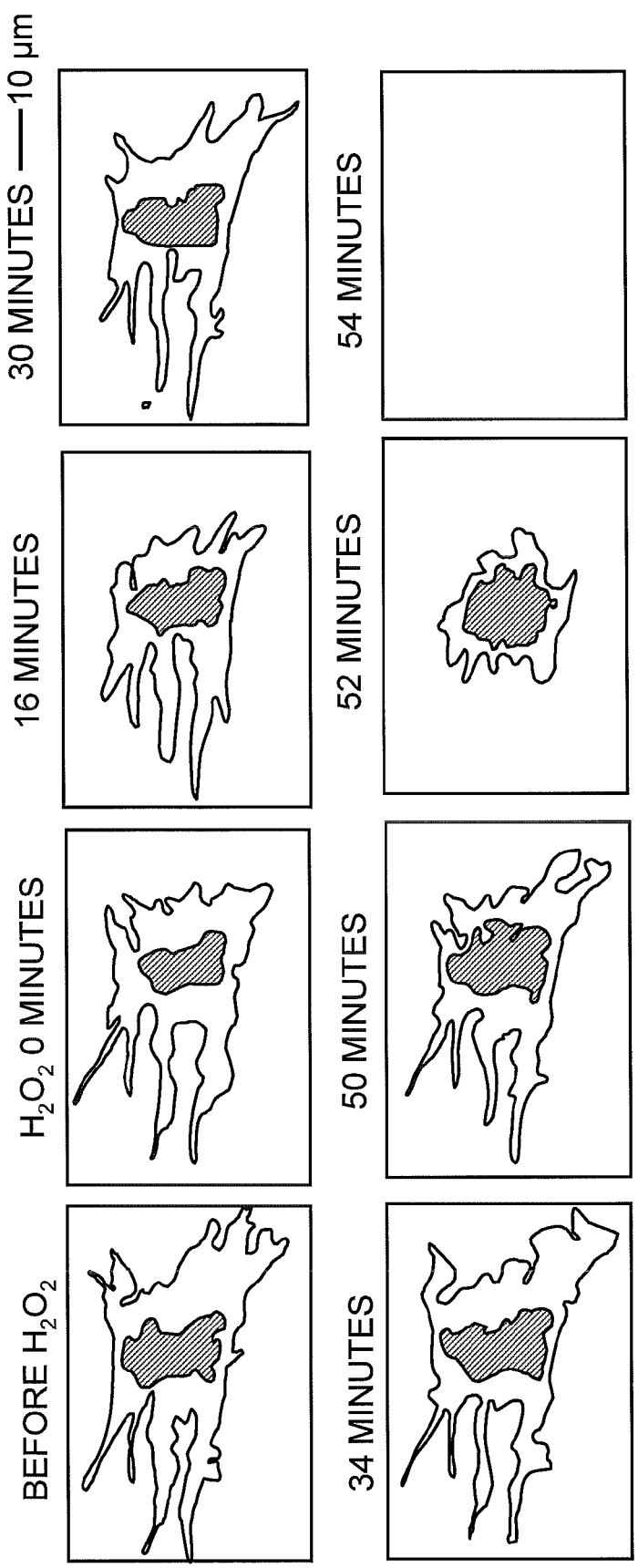

Time-lapse traces of tetrarethylrhodamine methyl ester (TMRE) fluorescence from cardiac myocytes after $H_2O_2$ treatment in control and glutathione choline ester (Mito GSH) pre-treated cells were obtained (FIG. 10). TMRM was used as an indicator of mitochondrial membrane potential. The myocytes were pretreated with 50 µM Mito GSH for 30 minutes and then washed to remove the antioxidant from the solution in which myocytes were suspended. In control, myocytes were not pretreated with any drug. TMRM was excited at 555 nm and fluorescence emission was detected at 590 nm. Fluorescence images were taken every 2 minutes to avoid photobleaching and phototoxicity. Myocytes were subjected to oxidative stress by adding 50 µM $H_2O_2$. In the control cell, the TMRM fluorescence was completely invisible 32 minutes after $H_2O_2$ treatment (FIG. 10A). However, in Mito GSH pretreated cell, the TMRM fluorescence persisted till 50 minutes (FIG. 10B). This experiment shows that Mito GSH pretreatment delayed $H_2O_2$-induced mitochondrial membrane depolarization.

Figure 11:
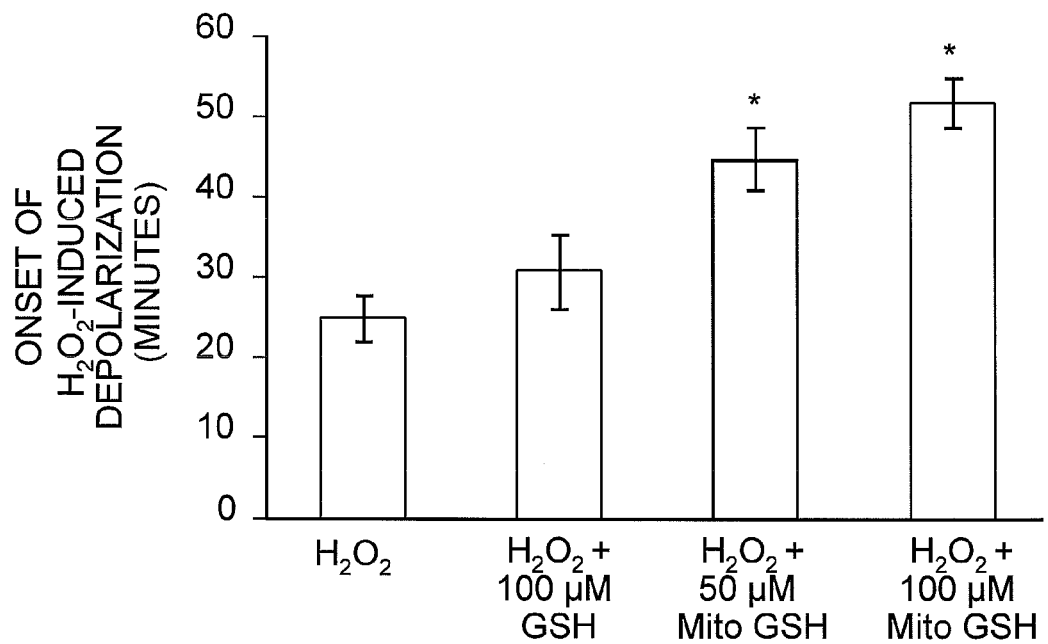
FIG. 11 graphically represents the latency of $H_2O_2$-induced depolarization of mitochondrial membrane potential in control ($H_2O_2$), glutathione (GSH), and glutathione choline ester (Mito GSH), demonstrating the ability of Mito GSH to delay the onset of $H_2O_2$-induced depolarization of cultured neonatal rat ventricular myocytes.

The latency of $H_2O_2$-induced depolarization of mitochondrial membrane potential in control ($H_2O_2$), glutathione (GSH), and glutathione choline ester (Mito GSH) is represented in FIG. 11. As shown, GSH (100 µM) did not significantly increase the time for onset of $H_2O_2$-induced depolarization. However, Mito GSH (50 and 100 µM) significantly enhanced the time for onset of $H_2O_2$-induced depolarization. Time for onset of $H_2O_2$-induced depolarization in Mito GSH (100 µM) pretreated myocytes was 53±3.6 min compared to 25±3.2 min for control myocytes. * p<0.05.

Figures 13, 14:
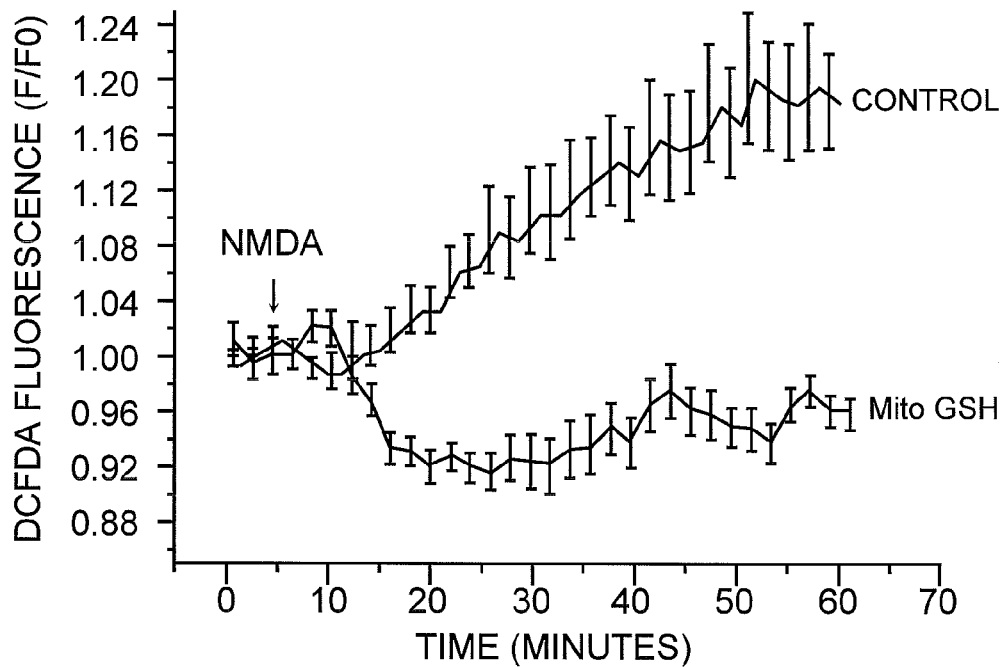
FIG. 13 demonstrates that glutathione choline ester (Mito GSH) protects against N-methyl-D-aspartate (NMDA)-induced reactive oxygen species generation in brain striatal neurons.
FIG. 14 demonstrates the effect of mitochondrial-targeted antioxidants upon onset of N-methyl-D-aspartate (NMDA, 100 µM)-induced depolarization of mitochondrial membrane of brain striatal neurons.

The ability of mitochondrial-targeted antioxidant N-acetyl-L-cysteine choline ester (mito NAC) to delay the onset of $H_2O_2$-induced depolarization of mitochondrial membrane potential in cultured neonatal rat ventricular myocytes was assessed (FIG. 13). Using identical conditions and treatment concentrations as presented in the example showing Mito GSH delays the onset of $H_2O_2$-induced depolarization, myocytes pretreated with Mito NAC showed a delayed onset of $H_2O_2$-induced depolarization and loss of fluorescence indicating a protective effect of this compound.

Example 10

Figure 12:
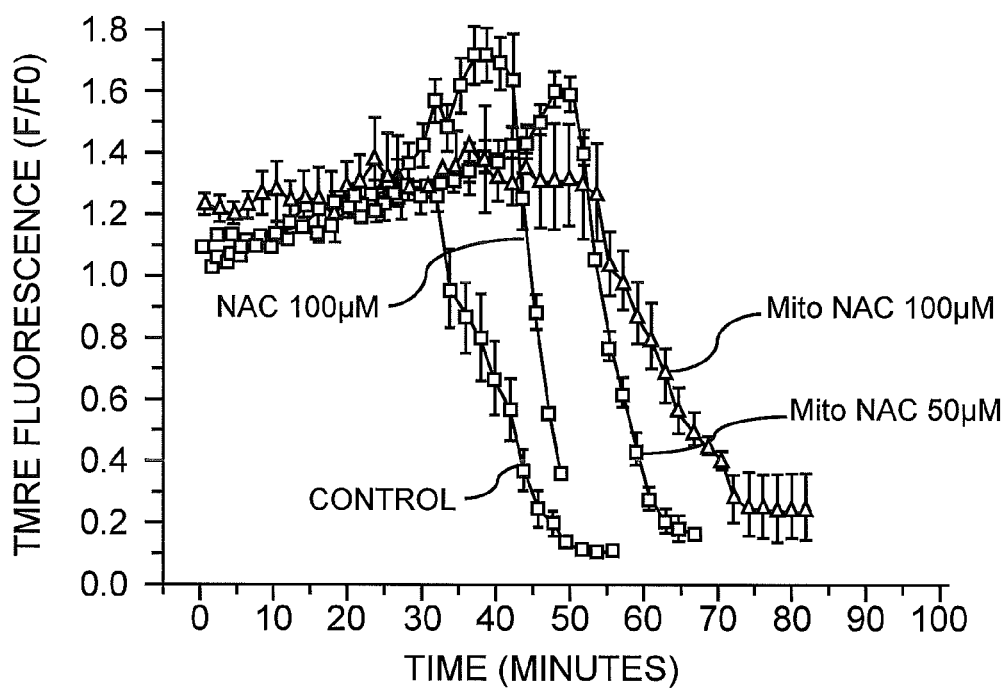
FIG. 12 demonstrates the ability of N-acetyl-L-cysteine choline ester (mito NAC) to delay the onset of $H_2O_2$-induced depolarization of mitochondrial membrane potential in cultured neonatal rat ventricular myocytes.

Mitochondrial-targeted Antioxidant Glutathione Choline Ester (Mito GSH) Protects Against N-Methyl-D-Aspartate (NMDA)-Induced Reactive Oxygen Species Generation in Brain Striatal Neurons Intracellular reactive oxygen species (ROS) were measured by using the redox-sensitive dye, dichlorohydrofluorescein ($H_2$DCFDA). The thiol-reactive chloromethyl group binds to cellular thiols trapping the dye inside the cell where oxidation converts it to the fluorescent form, dichlorofluorescein (DCF). Cultured striatal neurons (10 days in culture) were loaded with 50 nM $H_2$DCFDA for 25 min. The neurons were excited at 488 nm and the image was acquired at 515 nm wavelength. ROS production was induced by treating the neurons with 100 µM NMDA. An increase in DCFDA fluorescence by NMDA treatment reflected an increased production of ROS or oxidative stress. Pretreatment of neurons with 100 µM Mito GSH protected the neurons from ROS production (FIG. 12). Plots were normalized to baseline, and are shown as F/Fo, where F is the emitted fluorescence at any given time and Fo is the baseline fluorescence before addition of NMDA. Mito GSH pretreatment prevented NMDA-induced increase in ROS production. The traces were drawn from the mean values of 3 experiments.

The effects of mitochondrial-targeted antioxidants upon onset of N-methyl-D-aspartate (NMDA, 100 µM)-induced depolarization of mitochondrial membrane of brain striatal neurons were summarized in FIG. 14. Tetramethylrhodamine methyl ester (TMRM) was used as an indicator of mitochondrial membrane potential. The neurons were pretreated with either 50 µM glutathione (GSH) or glutathione choline ester (Mito GSH) or N-acetyl-L-cysteine (NAC) or N-acetyl-L-cysteine choline ester (Mito NAC) for 30 minutes and then washed to remove the antioxidants from the solution in which neurons were suspended. Control neurons were not pretreated with any drug.

Example 11

Inhibition of Ischemia-induced Neurological Damage and Inhibition of Reactive Oxygen Species In Vivo The compounds synthesized in Examples 1-2 will be administered to rats to assess their ability to attenuate ischemia/reperfusion injury to brain tissue caused by a focal cerebral ischemia model. Focal cerebral ischemia (45 min) will be induced in anesthetized rats using standard procedures (i.e., occluding the middle cerebral artery (MCA) with an intra-luminal suture through the internal carotid artery). Buffered solutions containing the compounds of the present invention will be administered pre-ischemia and post-ischemia to assess their efficacy. The rats will be scored post-reperfusion for neurological deficits and then sacrificed after 24 h of reperfusion. Infarct volume in the brain will be assessed by 2,3,5-triphenyl tetrazolium chloride (TTC). Brain sections will be immunostained for tumor necrosis factor (TNF-alpha) and inducible nitric oxide synthase

What is claimed:

1. A compound having the structural formula (I) or (II)

$$R-O-Z-\overset{Q^3}{\underset{Q^1}{N^+}}-Q^2 \quad\quad R-O-Z-\overset{Q^1}{\underset{Q^2}{\left\langle N^+\right.}}$$

Br⁻, I⁻, or Cl⁻          Br⁻, I⁻, or Cl⁻

(I)          (II)

wherein for both formula (I) and formula (II)

R is glutamyl, cysteinyl, N-acetyl-cysteinyl, glycyl, an acyl moiety derived from a 2,2-dialkylthiazolidine-4-carboxylic acid wherein alkyl is methyl or ethyl, L-γ-glutamylcysteinyl, L-γ-glutamylglycyl, L-cysteinylglycyl, L-γ-glutamyl-L-cysteinylglycyl, β-alanyl-L-histidyl, L-carnitinyl or acetyl-L-carnitinyl;

Z is (i) -$Z^1$-$Z^2$-,
(ii) -$Z^1$-O-$Z^2$-,
(iii) -$Z^1$-S-$Z^2$-,
(iv) -$Z^1$-N(H)-$Z^2$-,
(v) -$Z^1$-CO—N(H)-$Z^2$-, or
(vi) -$Z^1$-N(H)—CO-$Z^2$-,
wherein $Z^1$ is an aliphatic or non-aliphatic C1 to C10 hydrocarbon group; a single, fused or multi-ring aromatic group; or an aliphatic or non-aromatic cyclic group; and $Z^2$ is an aliphatic or non-aliphatic C1 to C10 hydrocarbon group; a single, fused or multi-ring aromatic group; or an aliphatic or non-aromatic cyclic group; and $Q^1$, $Q^2$, and $Q^3$ are independently aliphatic C1 to C5 hydrocarbon groups, or $Q^2$ and $Q^3$ together form an aliphatic N-heterocycle group;

wherein for formula (II), the aliphatic or non-aromatic N-heterocycle group bonded to variable Z by a carbon-carbon bond possesses a quaternary nitrogen.

2. The compound according to claim 1 wherein $Z^1$ is a direct link and $Z^2$ is an aliphatic or non-aliphatic C1 to C10 hydrocarbon group.

3. The compound according to claim 1 wherein $Z^1$ is a direct link and $Z^2$ is an aliphatic or non-aromatic cyclic group.

4. The compound according to claim 1 wherein $Z^1$ is an aliphatic or non-aliphatic C1 to C10 hydrocarbon group and $Z^2$ is an aliphatic or non-aliphatic C1 to C10 hydrocarbon group.

5. The compound according to claim 1 wherein $Z^1$ is an aliphatic or non-aliphatic C1 to C10 hydrocarbon group and $Z^2$ is an aliphatic or non-aromatic cyclic group.

6. The compound according to claim 1 wherein $Z^1$ is a single, fused or multi-ring aromatic group and $Z^2$ is an aliphatic or non-aliphatic C1 to C10 hydrocarbon group.

7. The compound according to claim 1 wherein $Z^1$ is a single, fused or multi-ring aromatic group and $Z^2$ is an aliphatic or non-aromatic cyclic group.

8. The compound according to claim 1 wherein $Z^1$ is an aliphatic or non-aromatic cyclic group and $Z^2$ is an aliphatic or non-aliphatic C1 to C10 hydrocarbon group.

9. The compound according to claim 1 wherein $Z^1$ is an aliphatic or non-aromatic cyclic group and $Z^2$ is an aliphatic or non-aliphatic cyclic group.

10. The compound according to claim 1 having a structure according to formula (I).

11. The compound according to claim 10 wherein $Q^1$, $Q^2$, and $Q^3$ are independently aliphatic C1 to C5 hydrocarbon group.

12. The compound according to claim 10 wherein $Q^2$ and $Q^3$ together form an aliphatic N-heterocycle group.

13. The compound according to claim 1 having a structure according to formula (II).

14. The compound according to claim 13 wherein $Q^2$ is present, and the N-heterocyclic possessing a quaternary nitrogen is, pyrrolidinyl, morpholinyl, or piperidinyl.

15. A pharmaceutical composition comprising a pharmaceutically acceptable carrier and a compound according to claim 1.

* * * * *